United States Patent [19]

Platz et al.

[11] 4,268,300
[45] May 19, 1981

[54] TRI/PENTA/AZA-TETRACYCLO-DODECA/ENES/DIENES OR-DECAENES

[75] Inventors: Rolf Platz, Mannheim; Werner Fuchs, Ludwigshafen; Norbert Rieber, Mannheim; Ulf-Rainer Samel, Mutterstadt; Johann Jung; Bruno Wuerzer, both of Limburgerhof, all of Fed. Rep. of Germany

[73] Assignee: BASF Aktiengesellschaft, Fed. Rep. of Germany

[21] Appl. No.: 112,789

[22] Filed: Jan. 16, 1980

Related U.S. Application Data

[62] Division of Ser. No. 781,767, Mar. 28, 1977, Pat. No. 4,189,434.

[30] Foreign Application Priority Data

Apr. 10, 1976 [DE] Fed. Rep. of Germany ....... 2615878

[51] Int. Cl.$^3$ .................... A01N 43/80; C07D 487/04
[52] U.S. Cl. .......................................... 71/76; 548/207
[58] Field of Search ............................ 548/207; 71/76

[56] References Cited

U.S. PATENT DOCUMENTS 3,707,364  12/1972  Becke et al. ...................... 548/207

Primary Examiner—Paul M. Coughlan, Jr.
Attorney, Agent, or Firm—Keil & Witherspoon

[57] ABSTRACT

New and valuable polycyclic compounds which contain nitrogen-containing rings and have a strong action on plants, agents for influencing plant growth containing these compounds, and a method of influencing plant growth with these compounds.

2 Claims, No Drawings

TRI/PENTA/AZA-TETRACYCLO-DODECA/ENES/DIENES OR-DECAENES

This is a division of application Ser. No. 781,767, filed Mar. 28, 1977, now U.S. Pat. No. 4,189,434.

The present invention relates to new and valuable polycyclic compounds, processes for their manufacture, crop protection agents containing these compounds, and their use as crop protection agents.

We have found that compounds of the formula

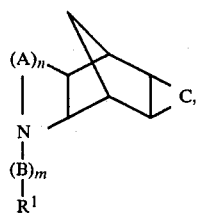

where A denotes the radical —N=N—, B denotes the radicals

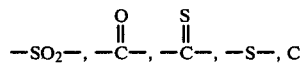

denotes the radicals

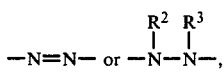

n denotes one of the integers 0 and 1, m denotes one of the integers 0 and 1, and $R^1$ denotes hydrogen, alkyl of 1 to 30 carbon atoms, alkenyl of 2 to 30 carbon atoms, alkynyl of 2 to 30 carbon atoms (preferably alkyl of 1 to 18 carbon atoms)—all of which may be linear or branched, cyclic or acyclic—, phenyl, naphthyl, or a more highly condensed aromatic radical, a heterocyclic radical with one or more hetero atoms (O, N, S), or aralkyl, it being possible for the aromatic radical to be substituted by a heterocycle, the abovementioned radicals, apart from hydrogen, being unsubstituted or mono- or polysubstituted by halogen (F, Cl, Br, I) or pseudo-halogen (CN, SCN), —OH, —SH, —NO$_2$, =N—OH, —N—OAlk(Ar),
=S, =NH, =NAlk(Ar), =O, —N—OH, —N—OAlk(Ar),
—COOH or —SO$_3$H or salts thereof, Alk(Ar)—O—,

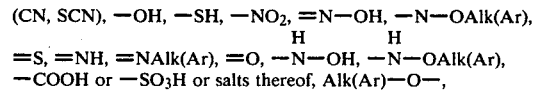

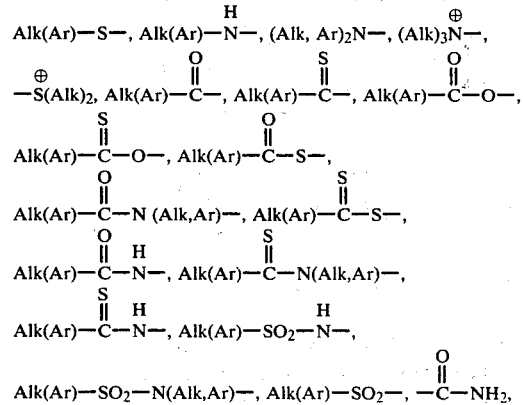

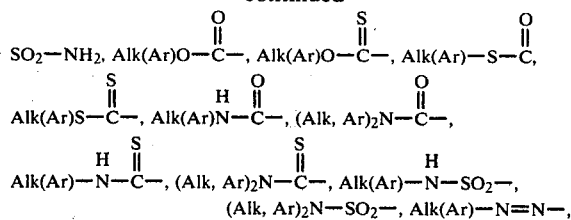

primary, secondary or tertiary alkyl, haloalkyl, haloalkoxy, haloalkylmercapto, or the radical

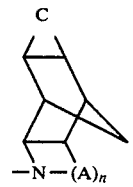

Alk denoting alkyl and Ar denoting an aromatic radical, and $R^1$ may additionally denote, when m is 0, (Alk, Ar)$_3$Si—, (Alk, Ar)$_3$SN— and, when m is 1, —OAlk(Ar), —SAlk(Ar), the radical

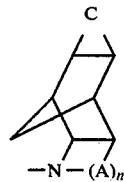

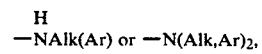

and $R^2$ and $R^3$ are identical or different and each denotes (B)$_m$—$R^4$, $R^4$ having the same meanings as $R^1$, and salts of these compounds, have a strong biological action on plants.

It is known to prepare compounds III-V, where R=CH$_3$— and C$_2$H$_5$—, by the following route: reaction of quadricyclane with azodicarboxylic acid esters (II) to give III, which is converted to IV by saponification and decarboxylation and oxidized, without isolation of IV, by CuCl$_2$ to the Cu$^I$ complex of the azo compound V (JACS, 91, 5668, 1969).

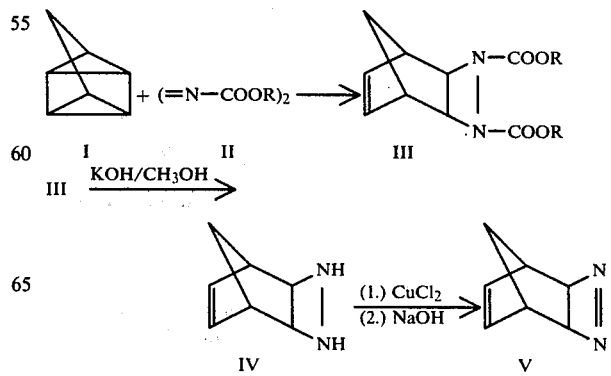

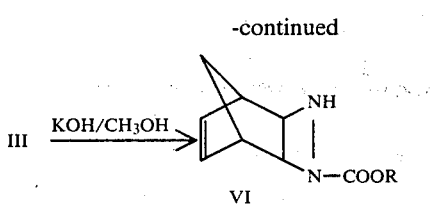

Compound VI is obtained by partial saponification and decarboxylation of III.

The active ingredients according to the invention may be prepared as follows:

1. Preparation of the compounds described in Examples 1 and 2 and the tables relating thereto. Reaction of compounds III-VI with alkyl, aryl, aralkyl, sulfonyl, silyl, stannyl or heterocyclic azides or diazides synthesized by known methods (Houben-Weyl, 10/3, 777).

The reaction takes place in an indifferent solvent, e.g., petroleum ether, benzene, xylene, methylene chloride, chloroform, chlorobenzene, ether, tetrahydrofuran, dioxane, dimethylformamide and mixture of solvents, such as dioxane/water, the solvent depending on the solubility of the azide employed, at from $-20°$ to $+180°$ C., preferably $+20°$ to $120°$ C. The reaction products precipitate out from the reaction solution either on cooling or, if polar solvents are used, upon addition of nonpolar solvents, or may be obtained by concentrating the solution.

During the reaction, $\Delta^2$-1,2,3-triazoline derivatives are formed, some of which, e.g., sulfonyl azides or azides in which the azide group is in conjugation with strongly electronegative substituents, already convert under the reaction conditions to exo- and/or endo-aziridine derivatives by elimination of nitrogen.

The addition of silyl azides to the C=C double bond gives N-silyl-$\Delta^2$-1,2,3-triazoline derivatives from which the corresponding N—H-$\Delta^2$-1,2,3-triazoline derivatives are formed upon treatment with ethanol/ligroin.

2. Preparation of the compounds described in Examples 3 and 4 and the tables relating thereto. Elimination of nitrogen from the $\Delta^2$-1,2,3-triazoline compounds to give the corresponding aziridine derivatives.

The elimination takes place in the abovementioned solvents either upon heating at from $90°$ to $140°$ C. or, after addition of acid catalysts, at from $20°$ to $80°$ C. Examples of suitable catalysts are acids (e.g., sulfuric acid, acetic acid, trifluoroacetic acid) and insoluble carrier substances containing acidic groups (e.g., ion exchangers).

3. Preparation of the compounds described in Example 5 and the table relating thereto. Reaction of N—H—$^2$-1,2,3-triazoline or N—H-aziridine derivatives with carboxylic or thiocarboxylic acid halides, carboxylic acid anhydrides, chlorocarbonates, thiochlorocarbonates, phosgene, sulfonyl halides, sulfenyl halides, alkyl halides, alkenyl halides, alkynyl halides, aralkyl halides, aldehydes, ketones, isocyanates, mustard oils, and carbamoyl and thiocarbamoyl halides, the corresponding N-substituted triazoline and aziridine derivatives being formed either by elimination of hydrogen halide or by addition of the N—H group to the C=O or C=N double bond.

The reactions are carried out in known manner in inert solvents and usually in the presence of bases, e.g., tertiary amines, alkali metal carbonates or bicarbonates, sodium methylate, alkali metal hydroxides, etc., at from $20°$ to $100°$ C.

4. The reaction of compounds IV and VI with the substances listed under (3) gives the corresponding N-substituted and N,N'-disubstituted derivatives (Example 6), which are then reacted as described above under (1) and (2) (Example 2, 4).

5. The reaction of quadricyclane with alkyl, aryl or aralkyl azodicarboxylic acid diesters gives the corresponding N,N'-disubstituted derivatives (Example 6), which are then reacted as described above under (1) and (2) (Example 2, 4).

Generally, the compounds may be prepared by any of the processes given under (1), (2) and (3) above. However, the process for which the individual examples and tables are given is usually the most advantageous of the various methods possible.

The structure of the active ingredients was confirmed by nmr, infrared and mass spectroscopy or ultimate analysis.

The melting points given are uncorrected.

EXAMPLE 1

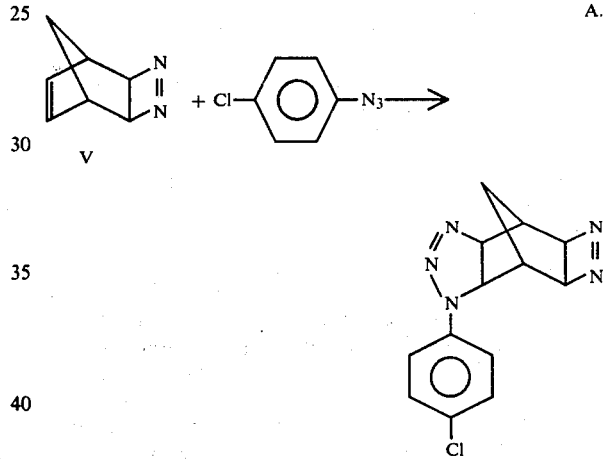

72 parts (by weight) of compound V and 92 parts of p-chlorophenylazide are heated in 240 parts of benzene for 5 hours at $80°$ C. After the mixture has cooled to room temperature, the $\Delta^2$-1,2,3-triazoline derivative which has formed is suction filtered and washed with 50 parts of petroleum ether; yield: 148 parts (90% of theory); m.p.: $192°-193°$ C. (decomposes).

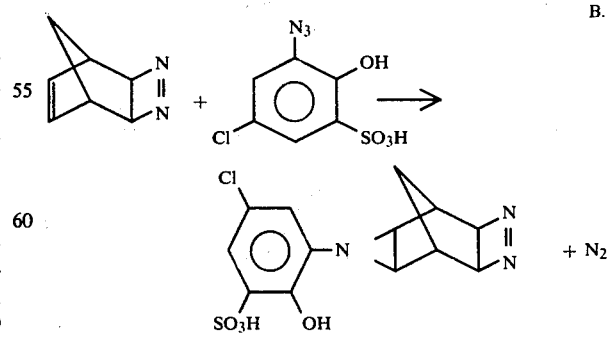

12 parts of V and 25 parts of 2-hydroxy-3-azido-5-chlorobenzenesulfonic acid are heated in 500 parts of dioxane/water (4:1) for 8 hours at $80°$ C. After the solvent has been distilled off in vacuo at 25 mbars, the residue is washed (digested) with 500 parts of benzene; yield: 32 parts (93% of theory); m.p.: 135° C. (decomposes).

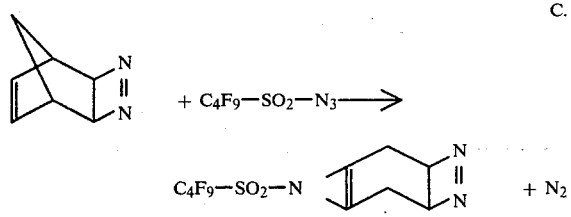

3 parts of V and 8.1 parts of perfluorobutylsulfonylazide are stirred in 15 parts of benzene for 20 hours at room temperature. After the benzene has been distilled off at 50 mbars, the residue is digested with 50 parts of petroleum ether; yield: 9 parts (86% of theory); m.p.: 115° C. (decomposes).

The following compounds were prepared analogously:

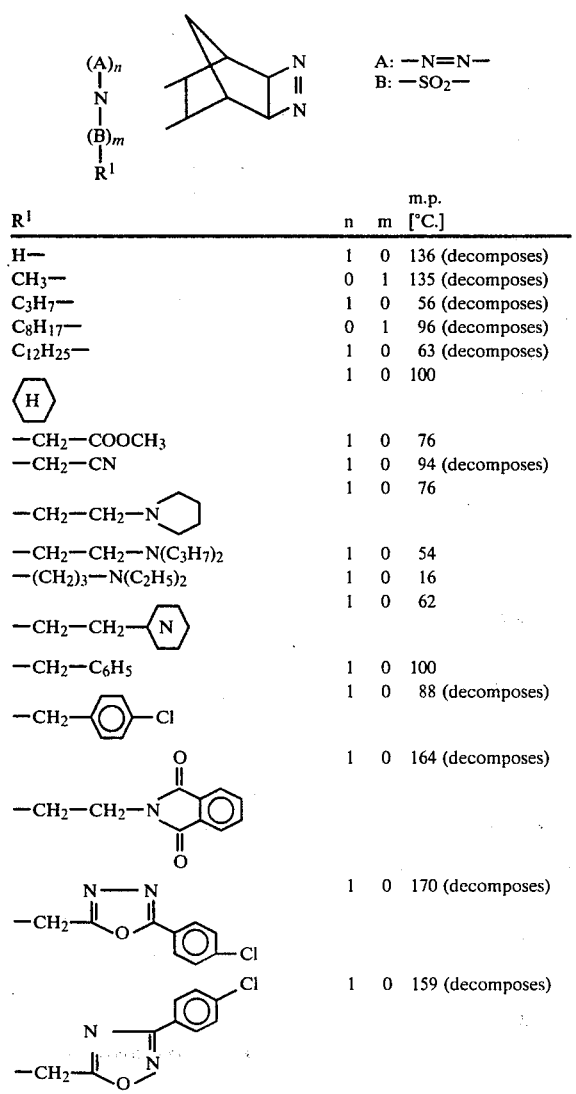

A: —N=N—
B: —SO$_2$—

| $R^1$ | n | m | m.p. [°C.] |
|---|---|---|---|
| H— | 1 | 0 | 136 (decomposes) |
| CH$_3$— | 0 | 1 | 135 (decomposes) |
| C$_3$H$_7$— | 1 | 0 | 56 (decomposes) |
| C$_8$H$_{17}$— | 0 | 1 | 96 (decomposes) |
| C$_{12}$H$_{25}$— | 1 | 0 | 63 (decomposes) |
| ⟨H⟩ | 1 | 0 | 100 |
| —CH$_2$—COOCH$_3$ | 1 | 0 | 76 |
| —CH$_2$—CN | 1 | 0 | 94 (decomposes) |
| —CH$_2$—CH$_2$—N⟨piperidine⟩ | 1 | 0 | 76 |
| —CH$_2$—CH$_2$—N(C$_3$H$_7$)$_2$ | 1 | 0 | 54 |
| —(CH$_2$)$_3$—N(C$_2$H$_5$)$_2$ | 1 | 0 | 16 |
| —CH$_2$—CH$_2$—⟨N⟩ | 1 | 0 | 62 |
| —CH$_2$—C$_6$H$_5$ | 1 | 0 | 100 |
| —CH$_2$—C$_6$H$_4$—Cl | 1 | 0 | 88 (decomposes) |
| —CH$_2$—CH$_2$—N(phthalimide) | 1 | 0 | 164 (decomposes) |
| —CH$_2$-(oxadiazole-C$_6$H$_4$-Cl) | 1 | 0 | 170 (decomposes) |
| —CH$_2$-(oxazole-C$_6$H$_4$-Cl) | 1 | 0 | 159 (decomposes) |

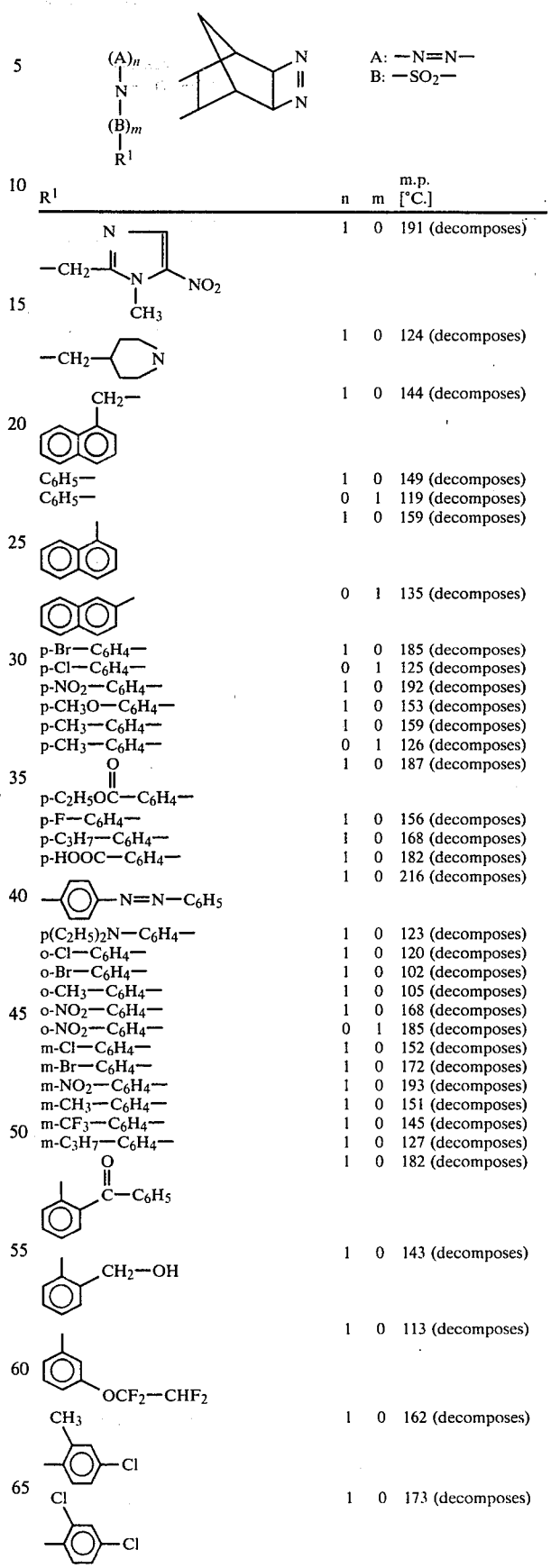

A: —N=N—
B: —SO$_2$—

| $R^1$ | n | m | m.p. [°C.] |
|---|---|---|---|
| —CH$_2$—(imidazole-CH$_3$)—C=CH—NO$_2$ | 1 | 0 | 191 (decomposes) |
| —CH$_2$—(piperidine) | 1 | 0 | 124 (decomposes) |
| —CH$_2$—(naphthyl) | 1 | 0 | 144 (decomposes) |
| C$_6$H$_5$— | 1 | 0 | 149 (decomposes) |
| C$_6$H$_5$— | 0 | 1 | 119 (decomposes) |
| (methylnaphthyl) | 1 | 0 | 159 (decomposes) |
| (methylnaphthyl) | 0 | 1 | 135 (decomposes) |
| p-Br—C$_6$H$_4$— | 1 | 0 | 185 (decomposes) |
| p-Cl—C$_6$H$_4$— | 0 | 1 | 125 (decomposes) |
| p-NO$_2$—C$_6$H$_4$— | 1 | 0 | 192 (decomposes) |
| p-CH$_3$O—C$_6$H$_4$— | 1 | 0 | 153 (decomposes) |
| p-CH$_3$—C$_6$H$_4$— | 1 | 0 | 159 (decomposes) |
| p-CH$_3$—C$_6$H$_4$— | 0 | 1 | 126 (decomposes) |
| p-C$_2$H$_5$OC(O)—C$_6$H$_4$— | 1 | 0 | 187 (decomposes) |
| p-F—C$_6$H$_4$— | 1 | 0 | 156 (decomposes) |
| p-C$_3$H$_7$—C$_6$H$_4$— | 1 | 0 | 168 (decomposes) |
| p-HOOC—C$_6$H$_4$— | 1 | 0 | 182 (decomposes) |
| —C$_6$H$_4$—N=N—C$_6$H$_5$ | 1 | 0 | 216 (decomposes) |
| p-(C$_2$H$_5$)$_2$N—C$_6$H$_4$— | 1 | 0 | 123 (decomposes) |
| o-Cl—C$_6$H$_4$— | 1 | 0 | 120 (decomposes) |
| o-Br—C$_6$H$_4$— | 1 | 0 | 102 (decomposes) |
| o-CH$_3$—C$_6$H$_4$— | 1 | 0 | 105 (decomposes) |
| o-NO$_2$—C$_6$H$_4$— | 1 | 0 | 168 (decomposes) |
| o-NO$_2$—C$_6$H$_4$— | 0 | 1 | 185 (decomposes) |
| m-Cl—C$_6$H$_4$— | 1 | 0 | 152 (decomposes) |
| m-Br—C$_6$H$_4$— | 1 | 0 | 172 (decomposes) |
| m-NO$_2$—C$_6$H$_4$— | 1 | 0 | 193 (decomposes) |
| m-CH$_3$—C$_6$H$_4$— | 1 | 0 | 151 (decomposes) |
| m-CF$_3$—C$_6$H$_4$— | 1 | 0 | 145 (decomposes) |
| m-C$_3$H$_7$—C$_6$H$_4$— | 1 | 0 | 127 (decomposes) |
| o-(C(O)C$_6$H$_5$)-C$_6$H$_4$— | 1 | 0 | 182 (decomposes) |
| o-(CH$_2$OH)-C$_6$H$_4$— | 1 | 0 | 143 (decomposes) |
| m-(OCF$_2$—CHF$_2$)-C$_6$H$_4$— | 1 | 0 | 113 (decomposes) |
| (3-CH$_3$, 4-Cl)-C$_6$H$_3$— | 1 | 0 | 162 (decomposes) |
| (2,4-Cl$_2$)-C$_6$H$_3$— | 1 | 0 | 173 (decomposes) |

-continued

| R¹ | n | m | m.p. [°C.] |
|---|---|---|---|
| 4-nitro-2-methylphenyl (with Cl) — 2-chloro-4-nitrophenyl-methyl | 1 | 0 | 141 (decomposes) |
| 2,4-dichlorophenyl-methyl | 1 | 0 | 127 (decomposes) |
| 4-trifluoromethyl-2-chlorophenyl | 1 | 0 | 152 (decomposes) |
| 2,3-dichlorophenyl | 1 | 0 | 78 (decomposes) |
| 3,5-dichlorophenyl | 1 | 0 | 186 (decomposes) |
| 2-chloro-4-nitrophenyl | 1 | 0 | 175 (decomposes) |
| 2,4-dichloro-5-methylphenyl | 1 | 0 | 129 (decomposes) |
| 2-methoxy-4-methylphenyl | 1 | 0 | 159 (decomposes) |
| 2,4-dimethylphenyl | 1 | 0 | 168 (decomposes) |
| 2-chloro-4-methylphenyl (with NO₂) | 1 | 0 | 166 (decomposes) |
| 2-methyl-4-nitrophenyl | 1 | 0 | 168 (decomposes) |
| 2-chloro-4-methoxyphenyl | 1 | 0 | 164 (decomposes) |
| 2,3-dibromophenyl (with NO₂, Cl) | 1 | 0 | 191 (decomposes) |
| 2,3-dichlorophenyl | 1 | 0 | 164 (decomposes) |

-continued

| R¹ | n | m | m.p. [°C.] |
|---|---|---|---|
| 2-hydroxy-5-methylphenyl | 1 | 0 | 131 (decomposes) |
| 3-methyl-4-methoxyphenyl | 1 | 0 | 189 (decomposes) |
| 4-methylsulfonyl-2-nitrophenyl | 0 | 0 | 187 (decomposes) |
| 2-hydroxy-5-methyl-3-carboxyphenyl | 0 | 0 | 255 (decomposes) |
| 2-chloro-5-methyl-4-sulfophenyl | 0 | 0 | 150 (decomposes) |
| 3,4-dichlorophenyl | 1 | 0 | 181 (decomposes) |
| 2-methoxy-3-methyl-4-chloro-5-methoxyphenyl | 1 | 0 | 136 (decomposes) |
| 2,5-diethoxy-4-benzamidophenyl | 1 | 0 | 196 (decomposes) |
| 2,4-dimethyl-3-chloro-5-methoxyphenyl | 1 | 0 | 184 (decomposes) |
| 6-methylnaphthalene-1-sulfonic acid | 0 | 0 | 250 (decomposes) |
| thiazol-2-yl | 1 | 0 | 136 (decomposes) |
| 1-phenylpyrazol-5-yl | 1 | 0 | 132 (decomposes) |
| pyridin-4-yl | 1 | 0 | 184 (decomposes) |

| $R^1$ | n | m | m.p. [°C] |
|---|---|---|---|
| (H₃C, CN, CH₃O-C(=O)-, S, thiophene structure) | 0 | 0 | 155 (decomposes) |
| (C₄H₉-NH-C(=N)-N=C(NH-C₂H₅)-N triazine) | 1 | 0 | 60 (decomposes) |
| (methylbenzisothiazole) | 1 | 0 | 188 (decomposes) |
| (methyl-nitro-benzisothiazole) | 0 | 0 | 150 (decomposes) |
| (methyl-benzodithiazolone) | 1 | 0 | 199 (decomposes) |
| (CH₃, N=N-aryl, =N-OH, C=O pyrazolone with p-tolyl) | 0 | 0 | 211 (decomposes) |
| (methyl-benzothiazole-p-tolyl) | 1 | 0 | 220 (decomposes) |
| (C₆H₅-C(=N)-N-O-C(=N)-aryl) | 1 | 0 | 147 (decomposes) |
| (C₆H₅, N-N, O, aryl) | 1 | 0 | 175 (decomposes) |
| (benzoyl-N-tolyl-N=CH-aryl) | 1 | 0 | 183 (decomposes) |
| (indazole methyl NH) | 1 | 0 | 183 (decomposes) |
| (C₆H₅-N, OH, =O, CH₃, pyridazinone) | 0 | 0 | 218 (decomposes) |
| (C₆H₅-C(=N-NH)-C(CH₃)=N) | 0 | 0 | 92 (decomposes) |
| (p-tolyl-N-N= bridged bicyclic with N=N) | 1 | 0 | 214 (decomposes) |
| (piperidino-CH₂-CH₂-CH₂-) | 1 | 0 | 69 (decomposes) |
| (pyrazole-cyclohexyl) | 1 | 0 | 138 (decomposes) |
| (pyrazole-CH₂-C₆H₅) | 1 | 0 | 112 (decomposes) |
| (CH₃, O₂N, Cl-phenyl) | 1 | 0 | 160 |

EXAMPLE 2

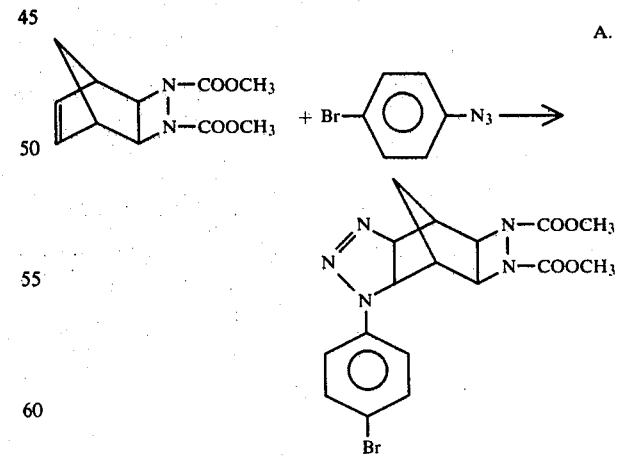

A.

24 parts of III and 20 parts of p-bromophenylazide are heated in 80 parts of benzene for 5 hours at 80° C. After the mixture has cooled to room temperature, the reaction product is suction filtered and washed with 50 parts of petroleum ether; yield: 38 parts (86% of theory); m.p.: 217°–218° C. (decomposes).

12 parts of III and 9 parts of phenylsulfonylazide are heated in 100 parts of chlorobenzene for 6 hours at 100° C. After the solvent has been distilled off at 25 mbars, the residue is digested with 100 parts of petroleum ether; yield: 18 parts (97% of theory); m.p.: 146° C. (ethanol/ligroin).

Compounds in which $R^2$ and/or $R^3$ denote H may also be present in the form of their salts, for instance as salts with mineral acids, e.g., as hydrochlorides.

The following compounds were prepared analogously:

B. 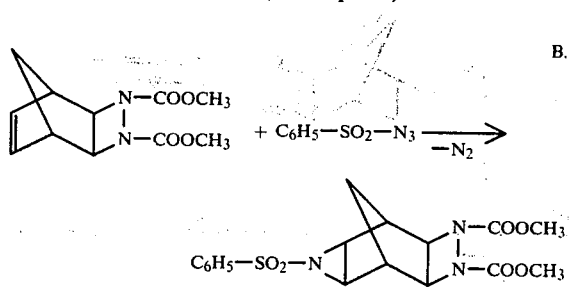

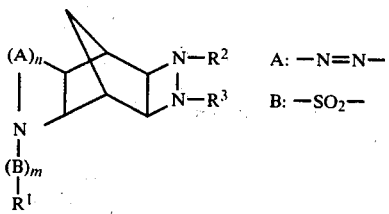

A: $-N=N-$
B: $-SO_2-$

| $R^1$ | $R^2$ | $R^3$ | n | m | m.p. °C. |
|---|---|---|---|---|---|
| H— | —COOCH$_3$ | —COOCH$_3$ | 1 | 0 | 83 (decomposes) |
| —H$_3$ | " | " | 0 | 1 | 100 (decomposes) |
| —C$_3$H$_7$ | " | " | 1 | 0 | 86 (decomposes) |
| —CH$_2$—COOCH$_3$ | " | " | 1 | 0 | 169 (decomposes) |
| —CH$_2$—C$_6$H$_5$ | " | " | 1 | 0 | 118 (decomposes) |
| C$_6$H$_5$— | " | " | 1 | 0 | 157 (decomposes) |
| " | —COOC$_2$H$_5$ | —COOC$_2$H$_5$ | 1 | 0 | 125 (decomposes) |
| " | H— | H— | 1 | 0 | 135 (decomposes) |
| Cl—C$_6$H$_4$— | " | " | | | |
| Br—C$_6$H$_4$— | " | " | 1 | 0 | 129 (decomposes) |
| Cl—C$_6$H$_4$— | ++H— | —COOCH$_3$ | 1 | 0 | 138 (decomposes) |
| Br—C$_6$H$_4$— | ++H— | —COOCH$_3$ | 1 | 0 | 85 (decomposes) |
| Cl—C$_6$H$_4$— | —COOCH$_3$ | —COOCH$_3$ | 1 | 0 | 212 (decomposes) |
| " | ++—COOCH$_3$ | —CH$_2$—C(O)—C$_6$H$_4$—Cl | 1 | 0 | 117 (decomposes) |
| " | ++—C(O)—N(H)—CH$_3$ | —COOCH$_3$ | 1 | 0 | 229 (decomposes) |
| " | ++—C(S)—N(H)—CH$_3$ | " | 1 | 0 | 217 (decomposes) |
| " | ++—C(S)—N(H)—C$_6$H$_5$ | " | 1 | 0 | 113 (decomposes) |
| " | ++—C(O)—S—CH$_2$—C(Cl)=Cl$_2$ | " | 1 | 0 | 84 (decomposes) |
| " | ++—SO$_2$—C$_6$H$_5$ | " | 1 | 0 | 139 (decomposes) |
| " | —C(O)—C$_6$H$_5$ | —C(O)—C$_6$H$_5$ | 1 | 0 | 210 (decomposes) |
| " | —COOCH$_2$—C$_6$H$_5$ | —COOCH$_2$—C$_6$H$_5$ | 1 | 0 | 70 (decomposes) |
| " | —COOC$_6$H$_5$ | —COOC$_6$H$_5$ | 1 | 0 | 173 (decomposes) |
| " | —COOC$_3$H$_7$ | —COOC$_3$H$_7$ | 1 | 0 | 150 (decomposes) |
| Cl—C$_6$H$_4$— | ++—COOCH$_3$ | —C(O)—(CH$_2$)$_7$CH=CH(CH$_2$)$_7$—CH$_3$ | 1 | 0 | oil |
| CH$_3$—C$_6$H$_4$—COOCH$_3$ | | —COOCH$_3$ | 1 | 0 | 221 (decomposes) |

-continued

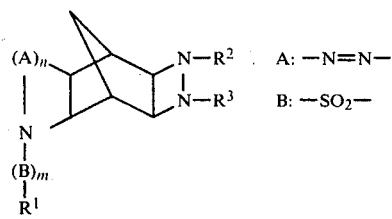

A: —N=N—
B: —SO₂—

| R¹ | R² | R³ | n | m | m.p. °C. |
|---|---|---|---|---|---|
| NO₂—⌬— | " | " | 1 | 0 | 197 (decomposes) |
| CH₃O—⌬— | " | " | 1 | 0 | 221 (decomposes) |
| ⌬(Cl) (ortho-Cl phenyl) | " | " | 1 | 0 | 88 (decomposes) |
| ⌬(NO₂) (ortho-NO₂ phenyl) | " | " | 1 | 0 | 180 (decomposes) |
| ⌬(CH₃) (ortho-CH₃ phenyl) | " | " | 1 | 0 | 163 (decomposes) |
| ⌬(CH₃) (meta-CH₃ phenyl) | " | " | 1 | 0 | 158 (decomposes) |
| ⌬(NO₂) (meta-NO₂ phenyl) | " | " | 1 | 0 | 206 (decomposes) |
| Cl,SO₃H,OH-substituted phenyl | " | " | 0 | 0 | 250 (decomposes) |
| 3-methyl-indazol-yl | " | " | 1 | 0 | 181 (decomposes) |
| Cl—⌬— | ++ —COOCH₃ | 3-(4-chlorophenyl)-1,2,4-oxadiazol-5-yl-methyl | 1 | 0 | 156 (decomposes) |
| naphthyl | —COOCH₃ | —COOCH₃ | 0 | 1 | 120 (decomposes) |
| benzothiazol-2-yl | H— | H— | 1 | 0 | 94 |

⁺⁺ isomer mixture; R² and R³ are interchangeable

EXAMPLE 3

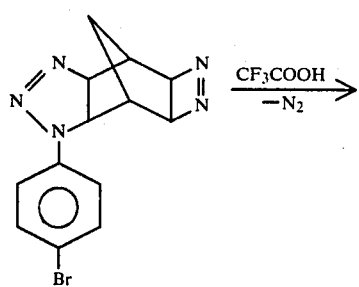

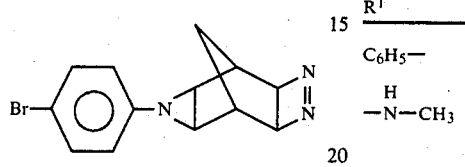

10 parts of the abovementioned $\Delta^2$-1,2,3-triazoline derivative and 3 parts of trifluoroacetic acid are stirred for 5 hours in 50 parts of methylene chloride at room temperature. After the solvent has been distilled off, the residue is digested with 30 parts of ether; yield: 8 parts (88% of theory); m.p.: 195° C. (decomposes) (benzene/ligroin).

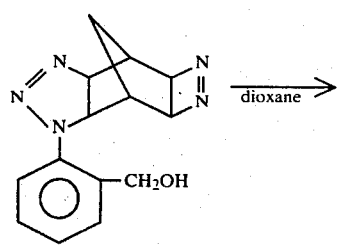

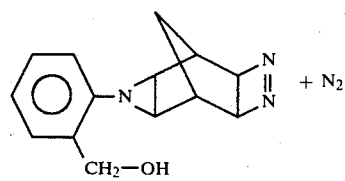

4 parts of the abovementioned $\Delta^2$-1,2,3-triazoline derivative is heated in 20 parts of dioxane for 6 hours at 100° C. After the solvent has been distilled off, the residue is digested with 10 parts of petroleum ether; yield: 3 parts (85% of theory); m.p.: 159° C. (decomposes) (ether/petroleum ether).

The following compounds were prepared analogously:

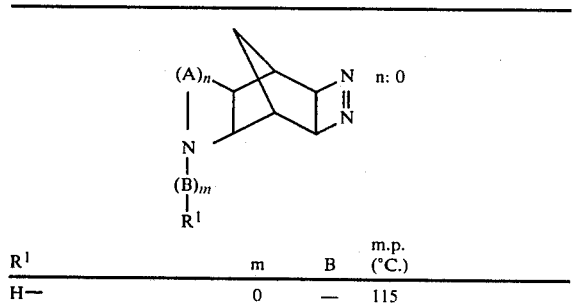

| $R^1$ | m | B | m.p. (°C.) |
|---|---|---|---|
| H— | 0 | — | 115 |
| $C_6H_5$— | 0 | — | 149 |
| $\underset{-N-CH_3}{H}$ | 1 | $-\underset{\|}{\overset{S}{C}}-$ | 80 |
| Cl—⟨○⟩— | 0 | — | 140 |
| HO—⟨○⟩— with CH₃ | 0 | — | 179 (decomposes) |
| $(C_2H_5)_2N$—⟨○⟩— | 0 | — | 122 (decomposes) |
| pyrazole-$C_6H_5$ | 0 | — | 126 (decomposes) |
| benzothiazole | 0 | — | 110 (decomposes) |
| benzodiazepinone-⟨○⟩— | 0 | — | 212 (decomposes) |
| ⟨○⟩—$CH_2$— | 0 | — | 66 |
| $CF_3$-⟨○⟩— | 0 | — | 169 (decomposes) |
| Cl,Cl-⟨○⟩— | 0 | — | 194 (decomposes) |
| benzothiazole | 0 | — | 203 (decomposes) |
| pyrazine | 0 | — | 146 |

EXAMPLE 4

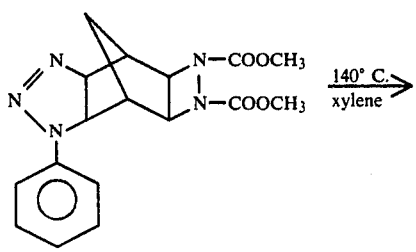

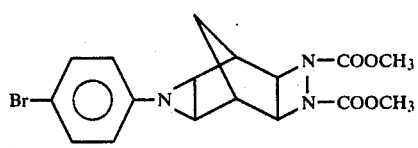

40 parts of the N-(p-bromophenyl)-Δ²-1,2,3-triazoline derivative is heated in 800 parts of xylene for 24 hours at 140° C. After the solvent has been distilled off, the residue is digested with 100 parts of petroleum ether; yield: 35 parts (92% of theory); m.p.: 170° C. (decomposes) (benzene/ligroin).

The following compounds were prepared analogously:

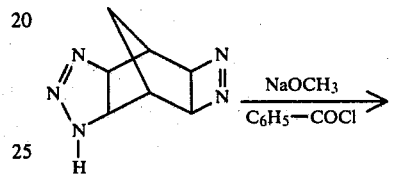

| R¹ | R² | R³ | m.p. (°C.) |
|---|---|---|---|
| $C_6H_5-CH_2-$ | $-COOCH_3$ | $-COOCH_3$ | 140 (decomposes) |
| $C_6H_5-$ | " | " | 187 |
| " | $-COOC_2H_5$ | $-COOC_2H_5$ | 109 |
| " | $-COOCH_3$ | $-COOCH_3$ | 168 |
| Cl—⟨○⟩— | | | |
| " | $-COOC_6H_5$ | $-COOC_6H_5$ | 117 |
| | $-COOCH_3$ | " | 174 |
| $CH_3$—⟨○⟩— | | | |
| " | " | " | 209 |
| $NO_2$—⟨○⟩— | | | |
| " | " | " | 153 |
| $CH_3O$—⟨○⟩— | | | |
| Cl ⟨○⟩— (ortho) | $-COOCH_3$ | $-COOCH_3$ | 197 |
| $CH_3$ ⟨○⟩— (ortho) | " | " | 175 |
| $NO_2$ ⟨○⟩— (ortho) | " | " | 178 |
| $CH_3$ ⟨○⟩— (meta) | " | " | 190 (decomposes) |
| $NO_2$ ⟨○⟩— (meta) | " | " | 258 (decomposes) |

EXAMPLE 5

A.

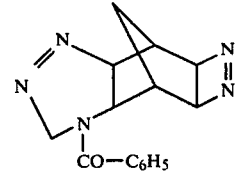

10 parts of the N-H-Δ²-1,2,3-triazoline derivative and 2 parts of sodium methylate are stirred in 100 parts of tetrahydrofuran for 1 hour at room temperature. 8.6 parts of benzoyl chloride is then dripped in and the mixture stirred for a further two hours. After the precipitate has been removed by suction filtration, the solvent is distilled off at 50 mbars and the residue digested with 30 parts of ether; yield: 13 parts (80% of theory); m.p.: 117° C. (decomposes).

B.

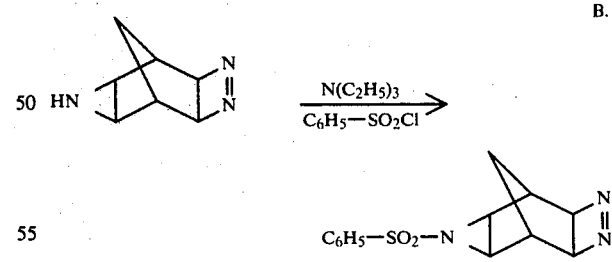

3 parts of the N-H-aziridine derivative and 3 parts of triethylamine are dissolved in 50 parts of tetrahydrofuran. At 0° to 5° C. and while stirring, 3.9 parts of benzene sulfochloride is dripped in. After removal of the precipitated triethylammonium chloride by suction filtration, the solvent is distilled off. The residue is washed with 50 parts of water and dried; yield: 5.4 parts (88% of theory); m.p.: 154° C. (decomposes).

The following compounds were prepared analogously:

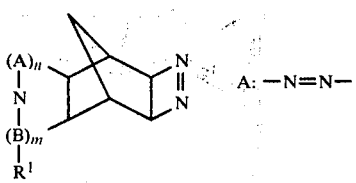

A: —N=N—

| R¹ | n | m | B | m.p. [°C] |
|---|---|---|---|---|
| —OCH₃ | 1 | 1 | —C(=O)— | 117 (decomposes) |
| —O—C₃H₇ | 1 | 1 | —C(=O)— | 118 (decomposes) |
| —O—⟨H⟩—C₄H₉ | 1 | 1 | —C(=O)— | 156 (decomposes) |
| H, —N—CH₃ | 1 | 1 | —C(=O)— | 169 (decomposes) |
| H, CH₃—N— | 0 | 1 | —C(=O)— | 118 (decomposes) |
| —N(CH₃)₂ | 1 | 1 | —C(=O)— | 108 (decomposes) |
| —CH₃ | 1 | 1 | —C(=O)— | 79 |
| H—C≡C—CH₂— | 1 | 0 | — | 60 |
| Cl—⟨C₆H₄⟩—C(=O)—CH₂— | 1 | 0 | — | 66 (decomposes) |
| Cl—⟨C₆H₄⟩—C(=N—O—)—CH₂— (with o-NO₂-phenyl) | 1 | 0 | — | 159 (decomposes) |
| (bis-triazoline structure) | 1 | 1 | —S— | 164 (decomposes) |
| (bis-triazoline with piperazine-C(=O) linker) | 1 | 1 | —C(=O)— | 270 (decomposes) |
| C₆H₅—NH— | 1 | 1 | —C(=O)— | 155 (decomposes) |
|  | 1 | 1 | —C(=O)— | 163 (decomposes) |

EXAMPLE 6

Preparation of the starting compounds

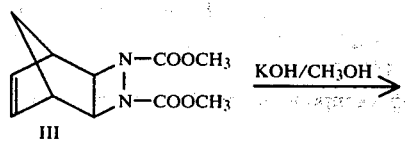

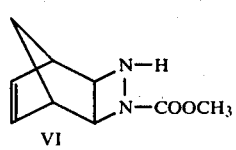

At 65° C. and while stirring, a solution of 35 parts of KOH in 60 parts of methanol is dripped into 60 parts of compound III and 50 parts of methanol. The reaction mixture is then stirred for a further 2 hours at 65° C. The solvent is subsequently distilled off at 50 mbars and the residue is extracted several times with a total of 1,200 parts of ether. After distilling off the ether, there is obtained 38 parts of compound VI (85% of theory; m.p. 94° C. from ligroin).

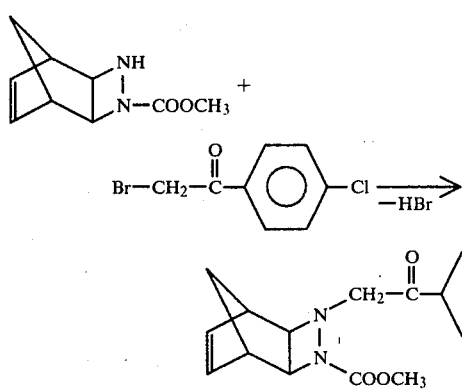

B.

5 parts of compound VI, 7 parts of p-chlorobromoacetophenone and 3 parts of soda are stirred in 150 parts of ether for 24 hours at 34° C. After suction filtration of the organic salts, the solvent and the residue are digested with 50 parts of petroleum ether; 9.5 parts (91% of theory); m.p.: 111° C. (benzene/ligroin).

C. 17 parts of compound VI and 8.7 parts of methyl mustard oil are heated in 200 parts of benzene for 5 hours at 80° C. After the solvent has been distilled off, the residue is digested with 100 parts of petroleum ether; yield: 25 parts (97% of theory); m.p.: 116° C. (ethanol/ligroin).

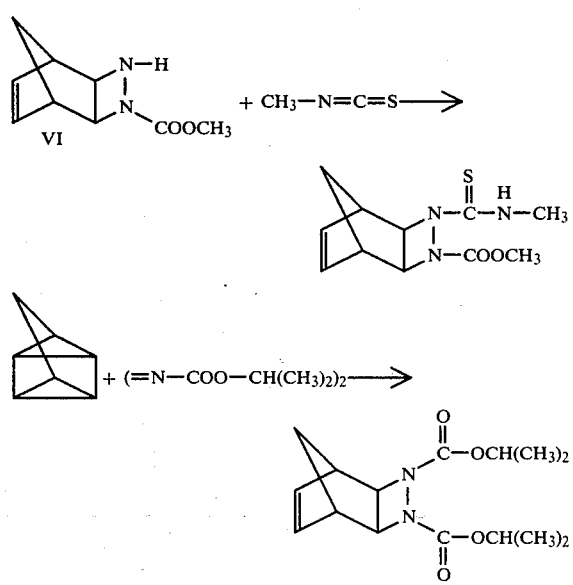

At 80° C., 40.5 parts of azodicarboxylic acid diisopropyl ester is dripped into 20 parts of quadricyclane in 100 parts of benzene. The mixture is then heated for 24 hours at 80° C. and the solvent subsequently removed at 50 mbars; yield: 58 parts (98% of theory) of an oil.

The compounds in which $R^2$ and/or $R^3$ denote H may also be present in the form of their salts, for instance as salts with mineral acids, e.g., as hydrochlorides.

The following compounds were prepared analogously:

| $R^2$ | $R^3$ | m.p. (°C.) |
|---|---|---|
| H— | $\overset{O}{\underset{}{-C-N-CH_3}}\overset{H}{}$ | 163 (decomposed) |
| —$CH_2$—$COOCH_3$ | —$COOCH_3$ | 76 |
| —$SO_2$—$C_6H_5$ | " | 130 |
| $-\overset{O}{\underset{}{C}}-\underset{}{\bigcirc}-Cl$ | " | 128 |
| $-\overset{O}{\underset{}{C}}-\overset{H}{N}-C_6H_5$ | " | 141 |
| $-\overset{S}{\underset{}{C}}-\overset{H}{N}-C_6H_5$ | " | 164 (decomposed) |
| $-\overset{O}{\underset{}{C}}-\overset{H}{N}-CH_3$ | " | 128 |
| H | " | b.p. 100/1 mba |
| $-\underset{OH}{\overset{}{C}}-CH_3$ | | |
| $-\overset{O}{\underset{}{C}}-S-CH_2-\overset{Cl}{\underset{}{C}}=CCl_2$ | " | 73 |
| $-\overset{O}{\underset{}{C}}-S-CH_2-C_6H_5$ | " | 75 |
| $-\overset{O}{\underset{}{C}}(CH_2)_7 \overset{H}{C}=\overset{H}{C}(CH_2)_7CH_3$ | " | oil |
| $-CH_2-\underset{O}{\overset{N}{\underset{}{\bigvee}}}\underset{N}{\overset{}{}}-\bigcirc-Cl$ | " | 135 |
| $C_6H_5—$ | $C_6H_5—$ | 98 |
| $C_6H_5—CH_2—$ | $C_6H_5—CH_2—$ | oil |

The compounds in Example 6 and the table were employed as starting compounds for active ingredient syntheses (cf. tables relating to Examples 2 and 4).

The new active ingredients have a strong biological action on plants, i.e., they influence plant growth, either by reducing the growth height, by changing the concentration of the plant constituents, or by destroying unwanted plants while not harming the crop plants.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acid, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients oils of various types, herbicides, fungicides, nematocides, insecticides, bactericides, trace elements, fertilizers, antifoams (e.g., silicones), and growth regulators.

Examples of herbicidally active compounds with which the active ingredients according to the invention may be combined are as follows:

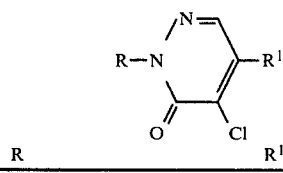

| R | $R^1$ |
|---|---|

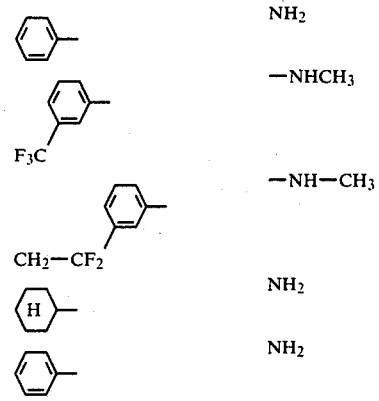

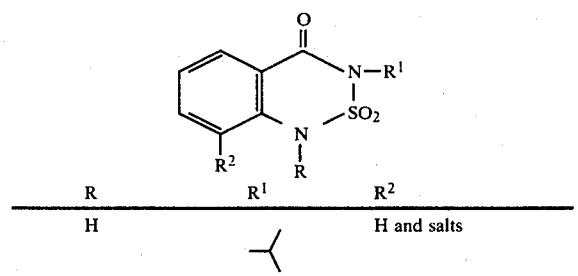

| R | $R^1$ | $R^2$ |
|---|---|---|
| H | -<( | H and salts |
| H | -<( | Cl and salts |
| H | -<( | F and salts |
| H | -<( | $CH_3$ and salts |
| $Cl_2OCH_3$ | -<( | H and salts |

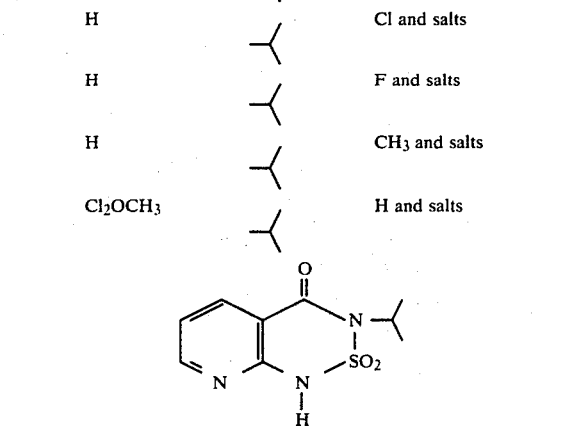

| $R^1$ | $R^2$ | $R^3$ |
|---|---|---|
| $CF_3$ | $nC_3H_7$ | $nC_3H_7$ |
| $CF_3$ | $nC_3H_7$ | $CH_2-CH_2Cl$ |
| $SO_2NH_2$ | $nC_3H_7$ | $nC_3H_7$ |

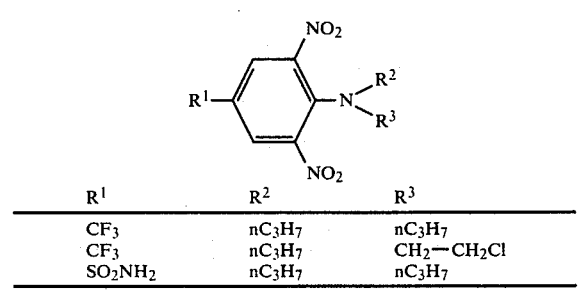

| $R^1$ | $R^2$ | $R^3$ |
|---|---|---|
| $CH_3$ | H | 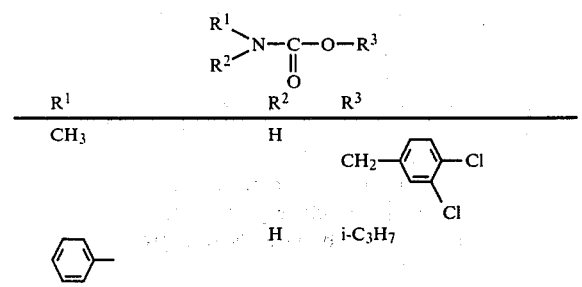 |
|  | H | $i-C_3H_7$ |

-continued

| | | |
|---|---|---|
| Ph— | H | —N=C(CH₃)₂ |
| Ph— | H | —CH(CH₃)C(O)NH—C₂H₅ |
| 3-Cl-C₆H₄— | H | i-C₃H₇ |
| 3-Cl-C₆H₄— | H | CH₂—C≡C—CH₂Cl |
| 3-Cl-C₆H₄— | H | —CH(CH₃)—C≡CH |
| 3,4-Cl₂-C₆H₃— | H | CH₃ |
| 4-H₂N-C₆H₄-SO₂— | H | CH₃ |

3-CF₃-C₆H₄-NH-C(O)-O-[2-methyl-5-(NHC(O)OCH₃)phenyl]

R¹-N(R²)-C(O)-[3-(NH-C(O)-O-R³)phenyl]

| R¹ | R² | R³ |
|---|---|---|
| Ph— | H | C₂H₅ |
| Ph— | CH₃ | CH₃ |
| 3,5-(H₃C)₂-C₆H₃— | H | CH₃ |
| 3-H₃C-C₆H₄— | H | C₂H₅ |
| 4-F-C₆H₄— | H | CH₃ |
| 3,5-(H₃C)₂-C₆H₃— | H | C₂H₅ |

R²(R¹)N—C(S)—S—R³

| R¹ | R² | R³ |
|---|---|---|
| i-C₃H₇ | i-C₃H₇ | CH₂—CCl=CHCl |
| n-C₃H₇ | n-C₃H₇ | C₂H₅ |
| " | " | n-C₃H₇ |
| sec. C₄H₉ | sec. C₄H₉ | C₂H₅ |
| C₂H₅ | C₂H₅ | CH₂-C₆H₄-Cl (4-) |
| cyclohexyl | C₂H₅ | C₂H₅ |
| 2-methylbicyclic | C₂H₅ | C₂H₅ | hexahydroazepine-N—C(O)—S—C₂H₅

4-methyl-hexahydroazepine-N—C(O)—S—R

| R |
|---|
| C₂H₅ |
| n-C₃H₇ |
| CH₂-Ph |

R¹-C(X)(Y)-C(O)-O-R²

| R¹ | X | Y | R² |
|---|---|---|---|
| CH₃ | Cl | Cl | Na |
| Cl | Cl | Cl | Na |
| C₂H₅ | Cl | Cl | Na |
| | Cl | H | CH₃ |
| 4-Cl-C₆H₄-CH₂— | H | H | H and salts |
| Ph-C(O)-N(O—)— | | | |
| Ph-CH(Cl)— | H | Cl | NH₄ |
| Ph-C(O)-N(3,4-Cl₂-C₆H₃)— | H | CH₃ | C₂H₅ |
| Ph-C(O)-N(3-Cl-4-F-C₆H₃)— | H | CH₃ | CH₃ |
| " | H | CH₃ | i-C₃H₇ |
| 4-Cl-C₆H₄-O-C₆H₄-O— | H | CH₃ | CH₂-CH(CH₃)₂ |
| 2,4-Cl₂-C₆H₃-O-C₆H₄-O— | H | CH₃ | CH₃ |

-continued

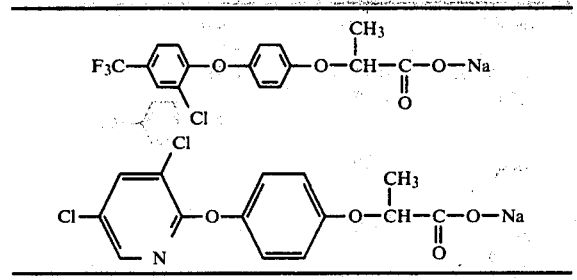

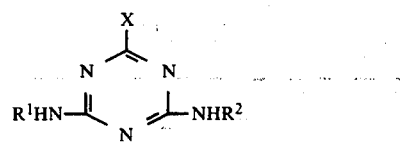

| R¹ | X | R² |
|---|---|---|
| i-C₃H₇ | Cl | C₂H₅ |
| " | Cl | |
| " | Cl | cyclopropyl |
| " | Cl | i-C₃H₇ |
| C₂H₅ | Cl | C₂H₅ |
| " | Cl | —C(CH₃)₂CN |
| " | Cl | —CH—CH₂—OCH₃ with CH₃ |
| " | Cl | —CH—C≡CH with CH₃ |
| " | Cl | —(CH₃)₂—CH |
| cyclopropyl | Cl | tert. C₄H₉ |
| i-C₃H₇ | OCH₃ | i-C₃H₇ |
| " | SCH₃ | C₂H₅ |
| C₂H₅ | SCH₃ | C₂H₅ |
| " | SCH₃ | tert. C₄H₉ |

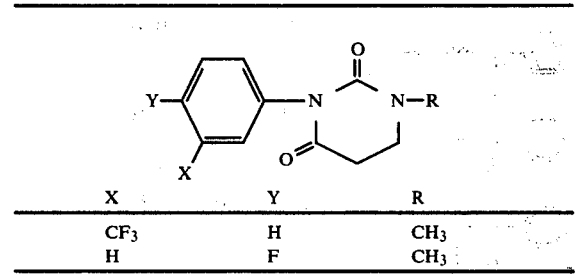

| X | Y | R |
|---|---|---|
| CF₃ | H | CH₃ |
| H | F | CH₃ |

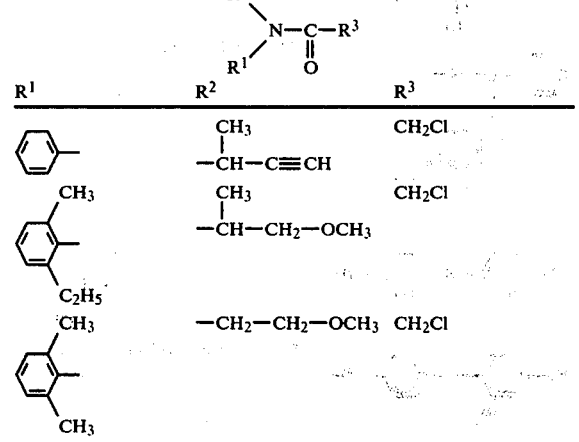

| R¹ | R² | R³ |
|---|---|---|
| phenyl | —CH(CH₃)—C≡CH | CH₂Cl |
| 2,6-(CH₃)(C₂H₅)phenyl | —CH(CH₃)—CH₂—OCH₃ | CH₂Cl |
| 2,6-(CH₃)₂phenyl | —CH₂—CH₂—OCH₃ | CH₂Cl |

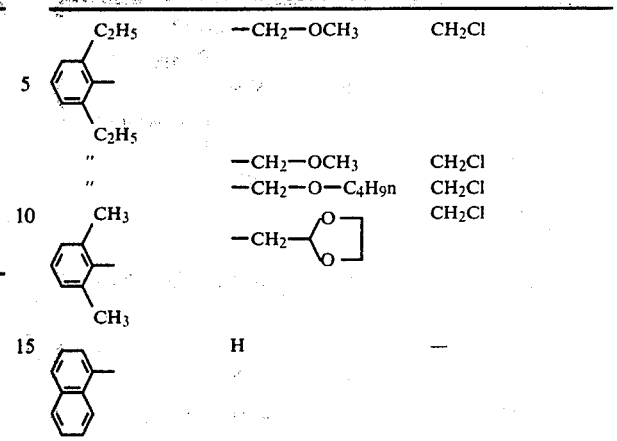

| | | |
|---|---|---|
| 2,6-(C₂H₅)₂phenyl | —CH₂—OCH₃ | CH₂Cl |
| " | —CH₂—OCH₃ | CH₂Cl |
| " | —CH₂—O—C₄H₉n | CH₂Cl |
| 2,6-(CH₃)₂phenyl | —CH₂—dioxolane | CH₂Cl |
| 1-naphthyl | H | — |
| 3,4-Cl₂phenyl | H | cyclopropyl |
| " | H | C₂H₅ |
| 4-Cl-phenyl | H | —C(CH₃)₂—C₃H₇ |
| 2-CH₃-5-CH₃ / F₃CSO₂NH-phenyl | H | CH₃ |
| 2,4-(CH₃)₂-5-F₃CSO₂NH-phenyl | H | CH₃ |
| HC≡C—C(CH₃)₂— | H | 3,5-Cl₂phenyl |

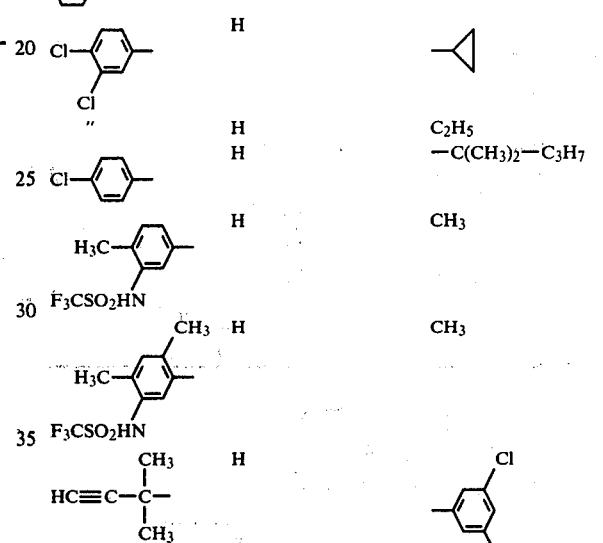

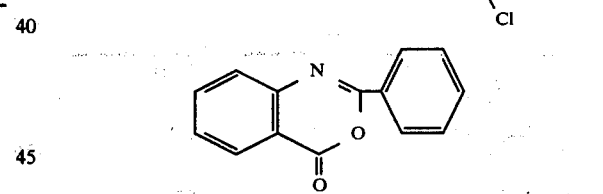

| X | X¹ | R |
|---|---|---|
| Br | Br | H and salts |
| I | I | H and salts |
| Br | Br | —C(=O)—(CH₂)₆—CH₃ |

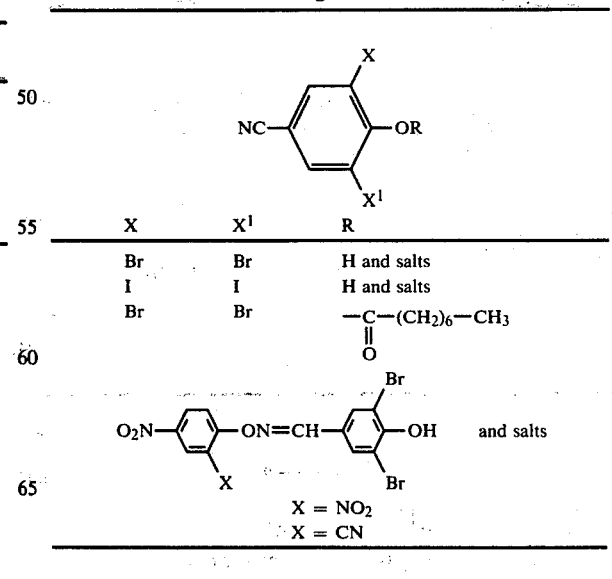

X = NO₂
X = CN

-continued
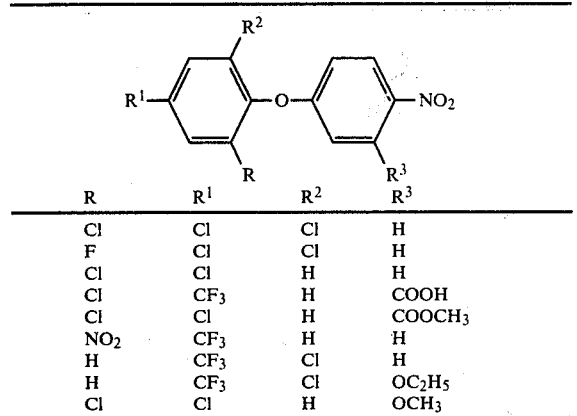
| R | R¹ | R² | R³ |
|---|---|---|---|
| Cl | Cl | Cl | H |
| F | Cl | Cl | H |
| Cl | Cl | H | H |
| Cl | CF₃ | H | COOH |
| Cl | Cl | H | COOCH₃ |
| NO₂ | CF₃ | H | H |
| H | CF₃ | Cl | H |
| H | CF₃ | Cl | OC₂H₅ |
| Cl | Cl | H | OCH₃ |
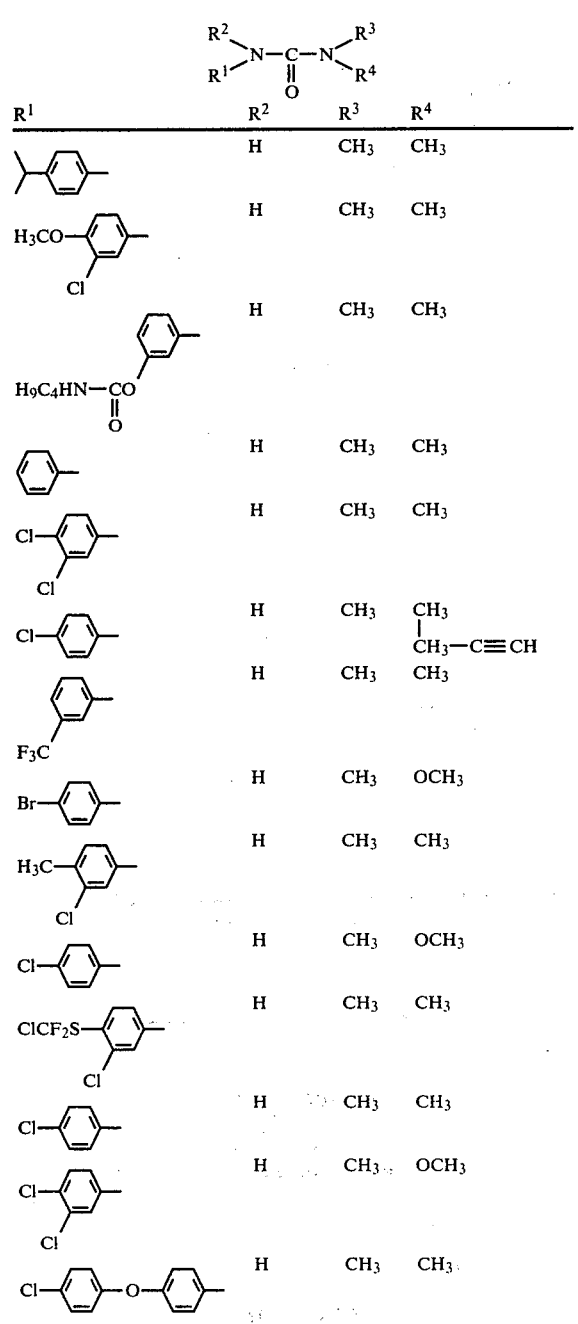
-continued
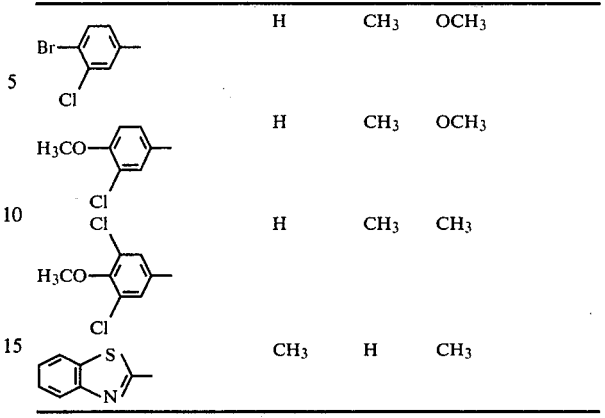
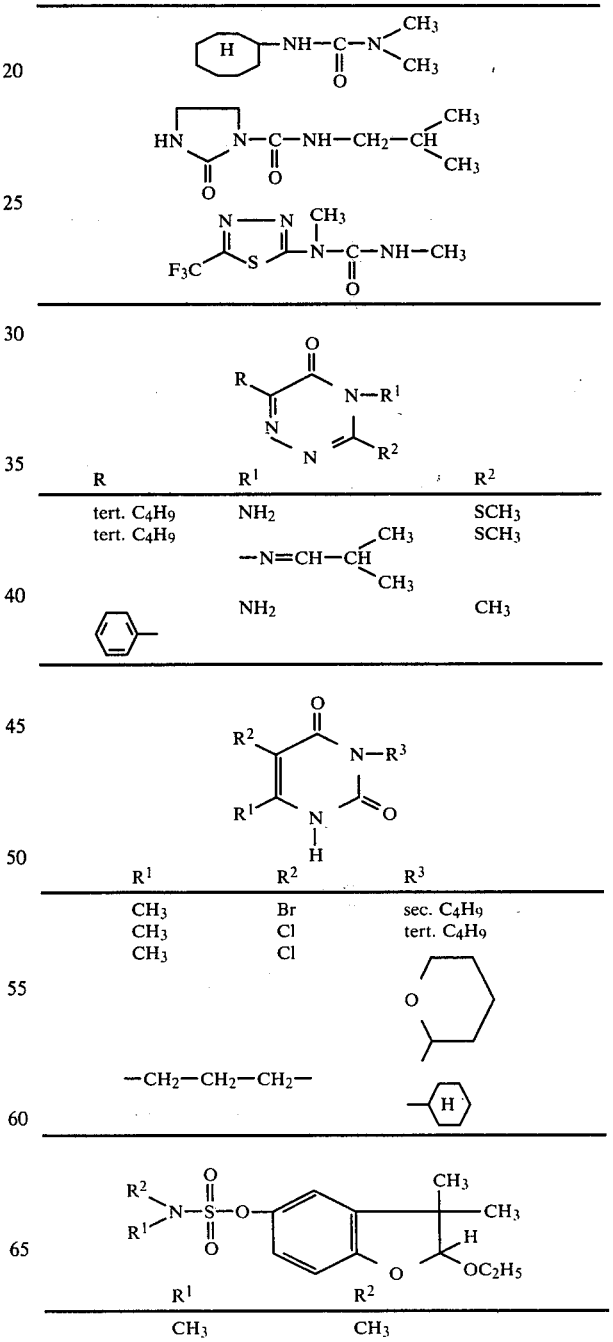

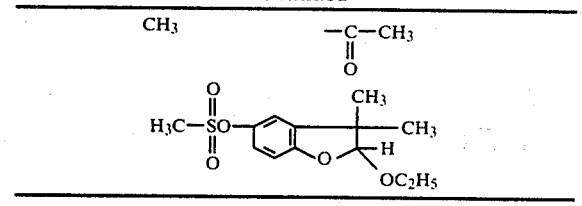
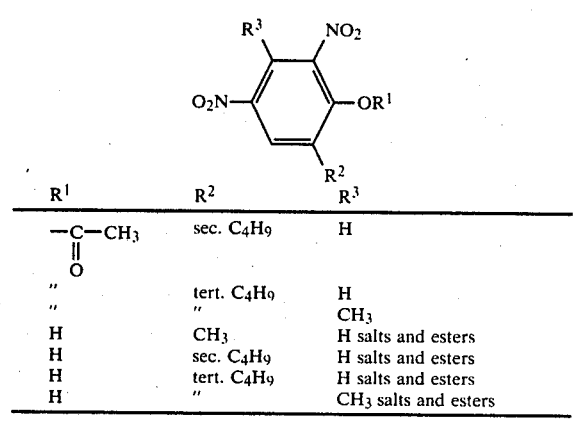
| $R^1$ | $R^2$ | $R^3$ | |
|---|---|---|---|
| $-\underset{\underset{O}{\parallel}}{C}-CH_3$ | sec. $C_4H_9$ | H | |
| " | tert. $C_4H_9$ | H | |
| " | " | $CH_3$ | |
| H | $CH_3$ | H | salts and esters |
| H | sec. $C_4H_9$ | H | salts and esters |
| H | tert. $C_4H_9$ | H | salts and esters |
| H | " | $CH_3$ | salts and esters |
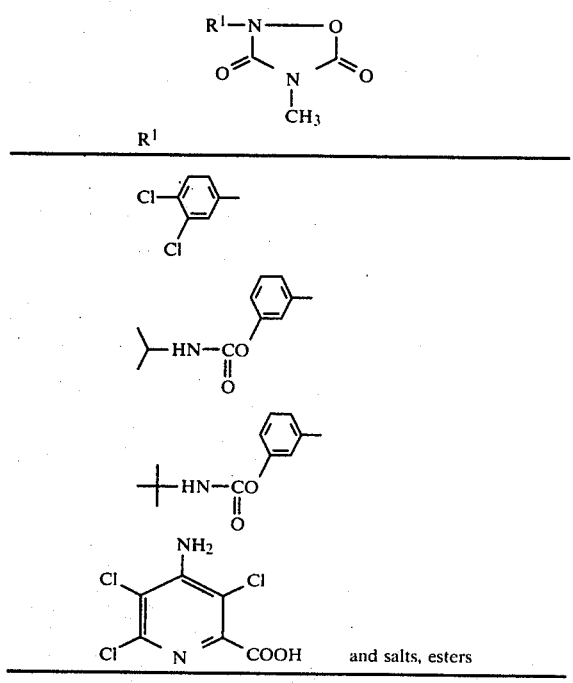
| $R^1$ | X |
|---|---|
| H | $CH_3OSO_3$ |
| Br | " |
| $CH_3$ | " |
| $CH_3$ | $CF_3SO_3$ |
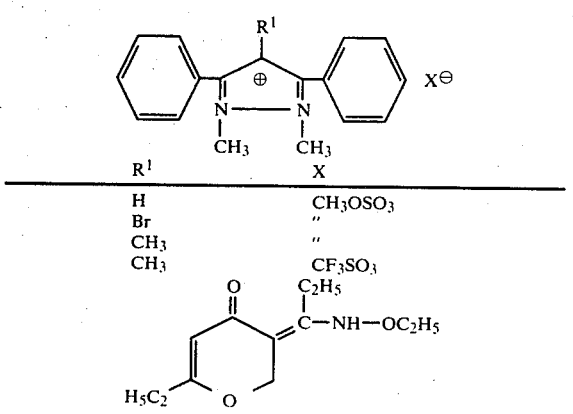
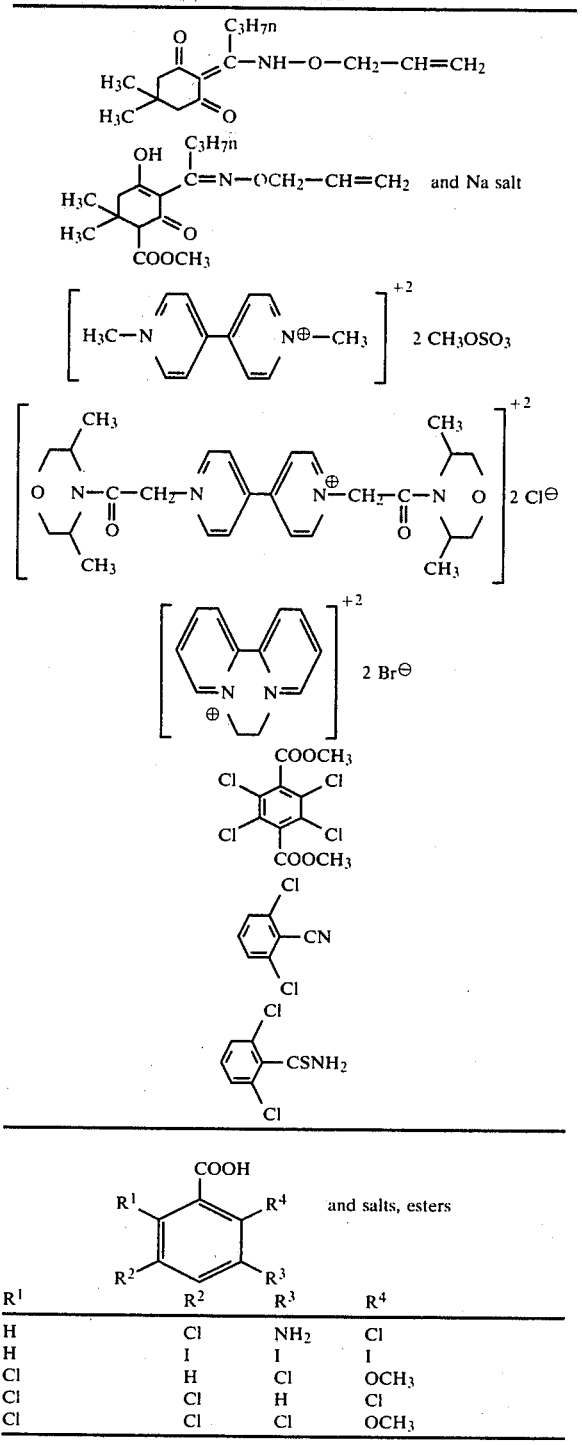
| $R^1$ | $R^2$ | $R^3$ | $R^4$ |
|---|---|---|---|
| H | Cl | $NH_2$ | Cl |
| H | I | I | I |
| Cl | H | Cl | $OCH_3$ |
| Cl | Cl | H | Cl |
| Cl | Cl | Cl | $OCH_3$ |
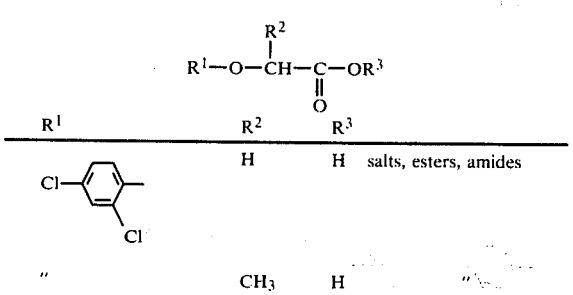
| $R^1$ | $R^2$ | $R^3$ |
|---|---|---|
| | H | H salts, esters, amides |
| Cl—⟨⟩—Cl | | |
| " | $CH_3$ | H " |

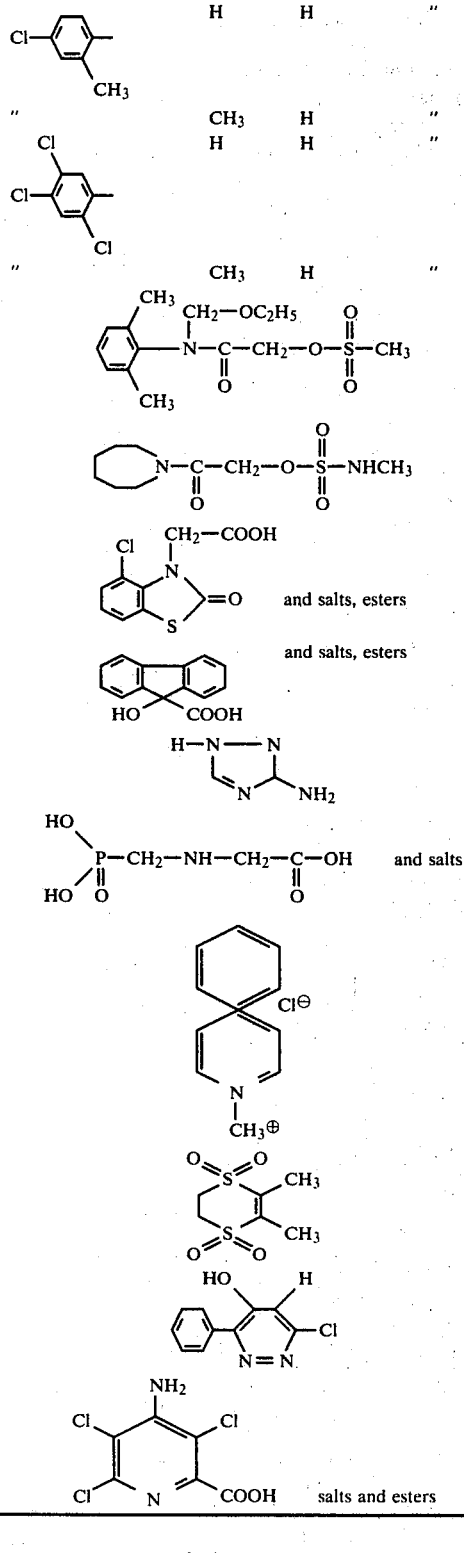
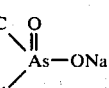
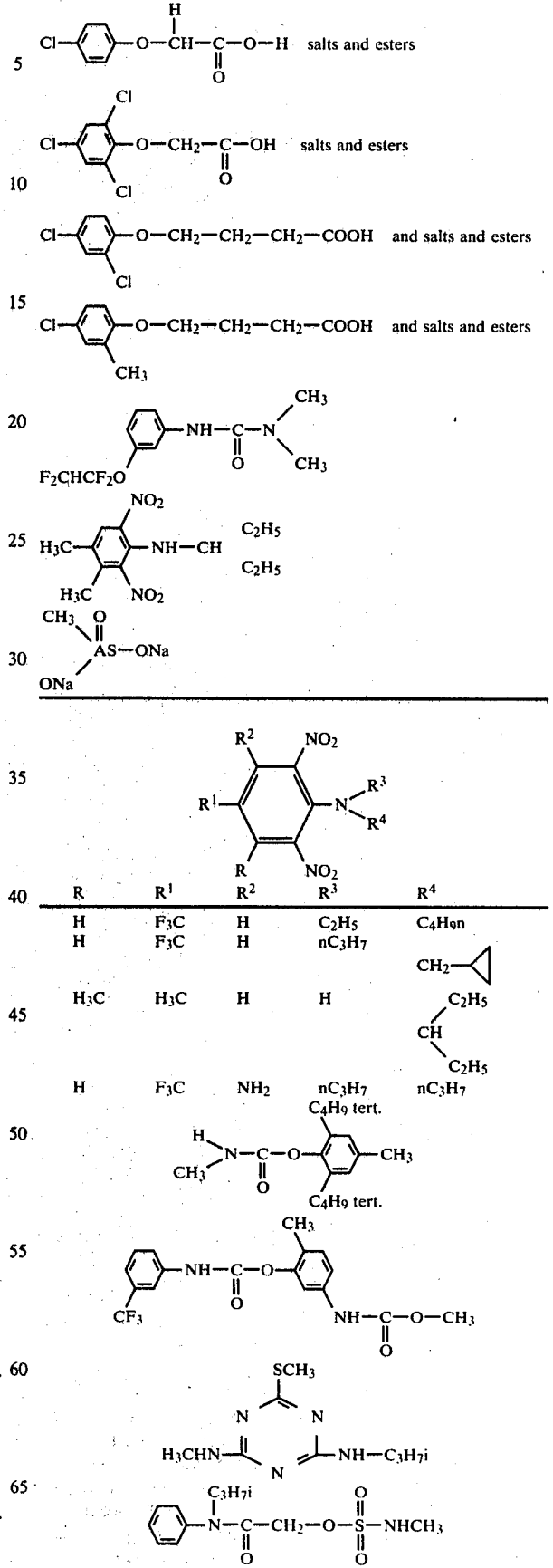

-continued

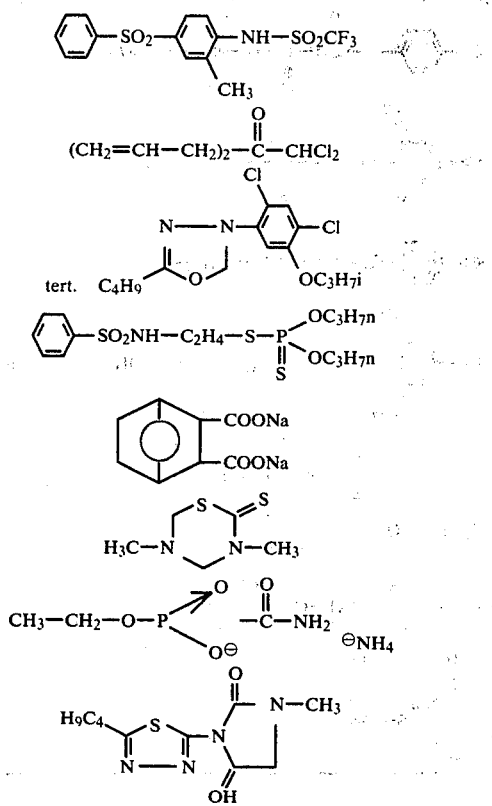

In many instances it may be advantageous to combine or mix the compounds according to the invention with other growth-regulating active ingredients, e.g., compounds of various chemical structure which form ethylene (e.g., phosphonic acid derivatives and silanes, ethyl hydrazines), and onium compounds (e.g., trimethylammonium, hydrazonium and sulfonium salts, and derivatives of morpholinium, piperidinium and pyridazinium compounds). Also of interest are other growth-regulating substances, for instance from the group of trifluoromethylsulfonamido-p-acetotoluidides, maleic hydrazide, abscisic acid derivatives, chlorinated phenoxy fatty acids having an auxinic action, and polyhydric alcohols and fatty acid esters having a specific action on meristematic tissue areas.

The amount used of the agents according to the invention may vary, and depends in the main on the type of effect desired.

The application rate is generally from 0.1 to 15 and more, preferably from 0.2 to 6, kg of active ingredient per hectare.

The agents according to the invention influence the growth of plant parts above and in the soil in a different manner; employed in the usual concentrations, they have a low toxicity to warm bloods.

The new agents have an effect on the physiology of plant growth and may be used for various purposes. The different effects of these active ingredients depend in essence on the time of application, based on the development stage of the seed or plant, and on the concentrations employed.

The influence on vegetative development is manifested in particular in a reduction in growth height, giving numerous plants, especially cereals, increased rigor and reducing the tendency toward lodging. Simultaneously, tillering is improved, resulting in an increase in ear-bearing stems per unit area.

In grass, the reduced growth height gives a denser, more resistant sward, this in particular enabling the mowing frequency to be reduced. This is a considerable labor-saving advantage for lawns, grass verges and in parks. The reduction in growth height is also accompanied by an increase in the chlorophyll content, as a result of which grass and other plants take on a much deeper green.

The influence on vegetative growth also considerably increases flowering and fruiting in numerous plants, e.g., cotton and soybeans.

Of particular importance is the surprising phenomenon that treatment with the substances according to the invention induces rooting. This results in a more rational use of water and nutrients by the treated plants, thus increasing their resistance not only to dryness but also to cold (frost).

The possibilities of using the compounds of the invention in fruit and ornamentals, in landscaping (including appropriate influence of the vegetation on barren land), and airfields and training grounds are varied and extensive.

The substances may also be successfully used for hastening ripening and flowering, and in special methods of cultivation.

The new agents may also positively influence the concentration of important plant constituents such as sugar and proteins.

The extent and degree of action depend on various factors, especially the time of application in relation to the development stage of the plant and the concentration employed. These factors are, in turn, different for different plant species and depend on the effect desired. For instance, lawns will be treated during the whole growth period; ornamentals in which it is desired to increase the bloom intensity and number of buds, before budding; and plants whose fruit is to used or processed, an appropriate length of time before the harvest. Various derivatives of the class of compounds described here have herbicidal properties, and are therefore suitable for removing and controlling unwanted plants.

EXAMPLES 7-10

Action on wheat, barley and oats

In the greenhouse, the four cereals wheat ("Opal" variety), rye ("Petkuser"), barley ("Villa") and oats ("Flämingskrone") were sown in plastic dishes 11.5 cm in diameter in a sandy loam adequately supplied with nutrients. The active ingredients were applied at various rates to the soil and to the leaves. When applied to the soil, the active ingredient were sprayed onto the surface of the soil on the day of sowing; in the case of leaf treatment, the leaves were sprayed in the usual manner at a growth height of the plants of 10 cm. During the 18 day growth period, the treated plants grew much more slowly than the untreated control, a fact later confirmed by measurements of the stem length. Measurements were taken of 100 plants from each series. As a result of the use of transparent plastic dishes it was surprisingly ascertained that root growth had been promoted in the treated series.

The prior art agent used for comparison purposes was N-2-chloroethyl-N,N,N-trimethylammonium cloride (CCC; German Printed Application DAS No. 1,294,734).

The results are given in the following tables.

EXAMPLE 7

Influence on the growth height of wheat (soil and leaf treatment)

| Active ingredient | Application rate kg/ha | Plant height in cm | relative |
|---|---|---|---|
| (A) Soil treatment | | | |
| Control | — | 31.0 | 100 |
| CCC | 0.5 | 26.0 | 83.9 |
| | 1.0 | 24.5 | 79.0 |
| | 2.0 | 22.5 | 72.6 |
| | 6.0 | 22.0 | 71.0 |
| (4-Cl-phenyl compound) | 0.5 | 28.5 | 91.9 |
| | 1.0 | 23.0 | 74.2 |
| | 2.0 | 20.5 | 66.1 |
| | 6.0 | 10.5 | 33.9 |
| (4-Br-phenyl compound) | 0.5 | 27.5 | 88.7 |
| | 1.0 | 22.5 | 72.6 |
| | 2.0 | 15.5 | 50.0 |
| | 6.0 | 11.5 | 31.7 |
| (B) Leaf treatment | | | |
| Control | — | 30.0 | 100 |
| CCC | 0.125 | 28.0 | 93.3 |
| | 0.5 | 26.0 | 86.7 |
| | 1.0 | 26.0 | 86.7 |
| | 2.0 | 23.0 | 76.7 |
| | 4.0 | 23.0 | 76.7 |
| (4-Cl-phenyl compound) | 0.125 | 24.0 | 80.0 |
| | 0.5 | 22.0 | 73.3 |
| | 1.0 | 20.0 | 66.6 |
| | 2.0 | 19.0 | 63.3 |
| | 4.0 | 17.5 | 58.3 |
| (4-Br-phenyl compound) | 0.125 | 25.0 | 83.3 |
| | 0.5 | 23.5 | 78.3 |
| | 1.0 | 21.0 | 70.0 |
| | 2.0 | 21.5 | 71.7 |
| | 4.0 | 20.0 | 66.7 |

EXAMPLE 8

Influence on the growth height of rye (soil and leaf treatment)

| Active ingredient | Application rate kg/ha | Plant height in cm | relative |
|---|---|---|---|
| (A) Soil treatment | | | |
| Control | — | 29.0 | 100 |
| CCC | 0.5 | 28.0 | 96.6 |
| | 1.0 | 27.5 | 94.8 |
| | 2.0 | 28.0 | 96.6 |
| | 6.0 | 26.5 | 91.4 |
| (4-Cl-phenyl compound) | 0.5 | 22.5 | 77.6 |
| | 1.0 | 19.0 | 65.5 |
| | 2.0 | 13.0 | 44.8 |
| | 6.0 | 8.5 | 29.3 |
| (4-Br-phenyl compound) | 0.5 | 23.0 | 79.3 |
| | 1.0 | 22.5 | 77.6 |
| | 2.0 | 19.0 | 65.5 |
| | 6.0 | 9.0 | 31.0 |
| (B) Leaf treatment | | | |
| Control | — | 29.5 | 100 |
| CCC | 0.125 | 29.0 | 98.3 |
| | 0.5 | 28.0 | 94.9 |
| | 1.0 | 27.5 | 93.2 |
| | 2.0 | 27.5 | 93.2 |
| | 4.0 | 29.0 | 98.3 |
| (4-Cl-phenyl compound) | 0.125 | 24.5 | 83.1 |
| | 0.5 | 20.0 | 67.8 |
| | 1.0 | 18.5 | 62.7 |
| | 2.0 | 17.5 | 59.3 |
| | 4.0 | 16.0 | 54.2 |
| (4-Br-phenyl compound) | 0.125 | 25.0 | 84.7 |
| | 0.5 | 20.5 | 69.5 |
| | 1.0 | 22.0 | 74.6 |
| | 2.0 | 18.0 | 61.0 |
| | 4.0 | 18.5 | 62.7 |

EXAMPLE 9

Influence on the growth height of barley (soil and leaf treatment)

| Active ingredient | Application rate kg/ha | Plant height in cm | relative |
|---|---|---|---|
| (A) Soil treatment | | | |
| Control | — | 31.5 | 100 |
| CCC | 0.5 | 28.0 | 88.9 |
| | 1.0 | 27.0 | 85.7 |
| | 2.0 | 26.0 | 82.5 |
| | 6.0 | 25.0 | 79.4 |
| [structure with Cl] | 0.5 | 28.0 | 88.9 |
| | 1.0 | 28.0 | 88.9 |
| | 2.0 | 23.5 | 74.6 |
| | 6.0 | 16.5 | 52.4 |
| [structure with Br] | 0.5 | 30.5 | 96.8 |
| | 1.0 | 29.0 | 92.1 |
| | 2.0 | 24.5 | 77.8 |
| | 6.0 | 19.0 | 60.3 |
| (B) Leaf treatment | | | |
| Control | — | 30.0 | 100 |
| CCC | 0.125 | 29.0 | 96.7 |
| | 0.5 | 28.5 | 95.0 |
| | 1.0 | 26.5 | 88.3 |
| | 2.0 | 27.0 | 90.0 |
| | 4.0 | 27.0 | 90.0 |
| [structure with Cl] | 0.125 | 24.0 | 80.0 |
| | 0.5 | 23.0 | 76.7 |
| | 1.0 | 21.5 | 71.7 |
| | 2.0 | 20.5 | 68.3 |
| | 4.0 | 18.5 | 61.7 |
| [structure with Br] | 0.125 | 25.5 | 85.0 |
| | 0.5 | 23.5 | 78.3 |
| | 1.0 | 22.0 | 73.3 |
| | 2.0 | 20.5 | 68.3 |
| | 4.0 | 20.0 | 66.7 | example 10

Influence on the growth height of oats (soil and leaf treatment)

| Active ingredient | Application rate kg/ha | Plant height in cm | relative |
|---|---|---|---|
| (A) Soil treatment | | | |
| Control | — | 28.0 | 100 |
| CCC | 0.5 | 28.0 | 100 |
| | 1.0 | 28.0 | 100 |
| | 2.0 | 27.0 | 96.4 |
| | 6.0 | 26.0 | 92.9 |
| [structure with Cl] | 0.5 | 25.0 | 89.3 |
| | 1.0 | 24.0 | 85.7 |
| | 2.0 | 21.0 | 75.0 |
| | 6.0 | 15.0 | 53.6 |
| [structure with Br] | 0.5 | 28.0 | 100 |
| | 1.0 | 26.5 | 94.6 |
| | 2.0 | 24.5 | 87.5 |
| | 6.0 | 15.5 | 55.4 |
| (B) Leaf treatment | | | |
| Control | — | 28.0 | 100 |
| CCC | 0.125 | 28.0 | 100 |
| | 0.5 | 28.5 | 101.8 |
| | 1.0 | 28.0 | 100 |
| | 2.0 | 27.0 | 96.4 |
| | 4.0 | 25.5 | 91.1 |
| [structure with Cl] | 0.125 | 23.5 | 83.9 |
| | 0.5 | 22.5 | 80.4 |
| | 1.0 | 21.0 | 75.0 |
| | 2.0 | 19.0 | 67.9 |
| | 4.0 | 17.0 | 60.7 |
| [structure with Br] | 0.125 | 25.5 | 91.1 |
| | 0.5 | 25.0 | 89.3 |
| | 1.0 | 22.5 | 80.4 |
| | 2.0 | 22.5 | 80.4 |
| | 4.0 | 22.0 | 78.6 |

EXAMPLE 11

Influence on stem length of cereals and Gramineae

The compounds listed in the following Tables A and B were examined by the method described below as to their effect on the crop plants listed in these tables:

The vessels used for the experiments were plastic pots having a volume of 1,130 cm³ (Table A) or paraffined paper cups having a volume of 170 cm³ (Table B). The pots and cups were filled with a sandy loam. The seeds of the test plants—separated by species—were sown shallow. Preemergence treatment (soil treatment) was effected immediately after sowing and before germination of the seeds. Seeds lying on the surface came into contact with the active ingredients. Postemergence treatment (leaf treatment) took place at an average growth height of the plants (depending on the rate of growth) of from 6 to 10 cm. The substances were suspended, emulsified or dissolved in water as diluent and applied by means of fine nozzles. The vessels were kept in the greenhouse in a temperature range of 12° C. to 25° C., and were regularly sprinkler irrigated for the duration of the experiment. The observation period was 6 to 8 weeks.

Results

Tables (A) and (B) contain compounds which exercise a strong influence on the development of the plant shoots. This growth inhibition of the parts of the plant above ground is desirable, and is not accompanied by disadvantageous symptoms such as chlorosis. The treated plants were usually conspicous for their dark green leaves.

EXAMPLE 11

TABLE (A)

Influence on the growth height of young cereal plants

| | | Growth height in cm after | | |
| | | soil treatment | leaf treatment | |
| Active ingredient | Application rate kg/ha | *Triticum aestivum* | *Hordeum vulgare* | *Triticum aestivum* |
|---|---|---|---|---|
| Control | — | 42 | 37 | 44 |
| [Cl—CH$_2$—CH$_2$—N$^\oplus$(CH$_3$)$_3$]Cl$^\ominus$ | 0.5 | 40 | 36 | 40 |
| | 1.0 | 40 | 31 | 40 |
| CCC (prior art) | 2.0 | 33 | 33 | 40 |
| (triazine-bicyclic, N-aryl: 3-Cl, 4-CF$_3$-phenyl) | 0.5 | 16 | 40 | 42 |
| | 1.0 | 15 | 39 | 27 |
| | 2.0 | 0 | 38 | 20 |
| (triazine-bicyclic, N-aryl: 2,4-diCl-phenyl) | 0.5 | 25 | 40 | 40 |
| | 1.0 | 25 | 38 | 34 |
| | 2.0 | 20 | 33 | 35 |
| (triazine-bicyclic, N-CH$_2$-(4-Cl-phenyl)) | 0.5 | 40 | 48 | 40 |
| | 1.0 | 40 | 44 | 39 |
| | 2.0 | 30 | 41 | 40 |
| (triazine-bicyclic, N-aryl: 3-Cl-phenyl) | 0.25 | 26 | — | 29 |
| | 0.5 | 15 | 43 | 25 |
| | 1.0 | — | 40 | 13 |
| | 2.0 | — | 30 | 12 |
| (triazine-bicyclic, N-aryl: 2-Br-phenyl) | 0.5 | 22 | 40 | 35 |
| | 1.0 | 12 | 42 | 33 |
| | 2.0 | 10 | 31 | 33 |
| (triazine-bicyclic, N-aryl: 3-Br-phenyl) | 0.5 | 24 | 38 | 33 |
| | 1.0 | 20 | 30 | 28 |
| | 2.0 | 16 | 27 | 17 |
| (triazine-bicyclic, N-aryl: 3-NO$_2$-phenyl) | 0.5 | 26 | 36 | 28 |
| | 1.0 | 26 | 36 | 28 |
| | 2.0 | 13 | 29 | 17 |

TABLE (A)-continued

Influence on the growth height of young cereal plants

| | | Growth height in cm after | | |
| | | soil treatment | leaf treatment | |
| Active ingredient | Application rate kg/ha | *Triticum aestivum* | *Hordeum vulgare* | *Triticum aestivum* |
|---|---|---|---|---|
| 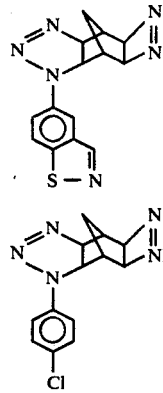 | 0.25 | 32 | — | 30 |
| | 0.5 | 28 | 36 | 23 |
| | 1.0 | 20 | 39 | 26 |
| | 2.0 | 23 | 31 | 20 |
| 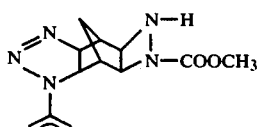 | 0.25 | 22 | 36 | 36 |
| | 0.5 | 12 | 30 | 30 |
| | 1.0 | 6 | 18 | 28 |
| | 2.0 | 7 | 14 | 25 |

TABLE (B)

Influence on the growth height of Gramineae (soil and leaf treatment)

| | | % growth inhibition compared with untreated control after | | | | | |
| | | soil treatment | | | leaf treatment | | |
| Active ingredient | Application rate kg/ha | *Avena sativa* | *Hordeum vulgare* | *Lolium multifl.* | *Avena sativa* | *Hordeum vulgare* | *Lolium multifl.* |
|---|---|---|---|---|---|---|---|
| [Cl—CH₂—CH₂—N(CH₃)₃]⁺Cl⁻ CCC (bekannt) | 3.0 | 25 | 10 | 5 | 45 | 10 | 20 |
| 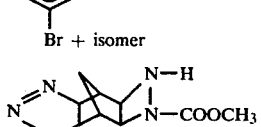 Br + isomer | 3.0 | 30 | 30 | 30 | 50 | 50 | 30 |
| 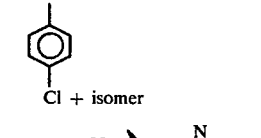 Cl + isomer | 3.0 | 20 | 0 | 0 | 40 | 35 | 20 |
| 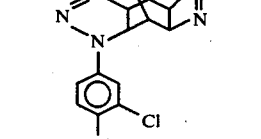 | 3.0 | 30 | 40 | 30+ | 40 | 30 | 25 |
| 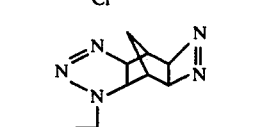 | 3.0 | 60 | 35 | — | 20 | 20 | 0 |

TABLE (B)-continued

| | | \% growth inhibition compared with untreated control after | | | | | |
|---|---|---|---|---|---|---|---|
| | | soil treatment | | | leaf treatment | | |
| Active ingredient | Application rate kg/ha | Avena sativa | Hordeum vulgare | Lolium multifl. | Avena sativa | Hordeum vulgare | Lolium multifl. |
| 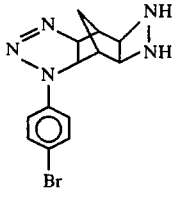 | 3.0 | 60 | 60 | 50 | 60 | 50 | 50 |
| 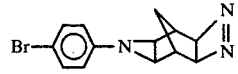 | 3.0 | 40 | 60+ | 50 | 50 | 50 | 50 |

0 = no inhibition
100 = no growth
+ = leaf necroses due to too high phytotoxicity

EXAMPLE 12

Action on stem length, number of lateral shoots and yield in spring barley

To examine the effect of the various substances on spring barley up to the maturity stage of the plants, an experiment was carried out in large pots. The plants were grown in quartz sand (fertilized with 2 g N as ammonium nitrate in 3 doses, 1 g $P_2O_5$ as secondary sodium phosphate, 1.5 g $K_2O$ as potassium sulfate, 0.5 g MgO as magnesium sulfate, 10 ml of a solution of trace elements, and 10 mg of iron as an iron complex). The active ingredients were applid to the leaves twice, once at a rate of 0.5 kg/ha and once at a rate of 1.5 kg/ha, at a plant height of 35 to 40 cm. The treated plants were up to 10% shorter than the control, and yields were also slightly up. The results of this experiment are given below.

EXAMPLE 13

Action on grass or lawns

Lawn seed of the standard mixture Agrostis tenius (10%), Cynosurus cristatus (10%), Festuca rubra (15%), Lolium perenne (35%) and Poa praetensis (30%) was sown in a loam in large pots. The soil was fertilized with 1.5 g N as ammonium nitrate and 1 g $P_2O_5$ as secondary potassium phosphate. After the grass had been cut twice, it was sprayed in conventional manner at a height of 4 cm with the active ingredients at various application rates. 19 days after treatment the growth height and dry substance content were determined. The treated grass was much shorter than the control, and produced a correspondingly lower amount of dry substance.

It was also observed that as the amount of compound according to the invention increased the color of the grass turned an intensive deep green. The results of this experiment are given below. The prior art compound used for comparison purposes was maleic hydrazide (M; German No. 815,192).

EXAMPLE 12

| | Influence on stem length, number of lateral shoots and yield in spring barley | | | | | |
|---|---|---|---|---|---|---|
| | | Stem length | | No. of lateral shoots | | Ear weight |
| Active ingredient | | cm | relative | no. | relative | g | relative |
| Control | | 76.9 | 100 | 93 | 100 | 90.4 | 100 |
| CCC | 3 kg/ha | 74.2 | 96.5 | 99 | 106.5 | 95.0 | 105.1 |
| 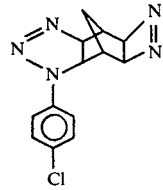 | 0.5 kg/ha | 74.1 | 96.4 | 105 | 112.9 | 91.5 | 101.2 |
| | 1.5 kg/ha | 69.7 | 90.6 | 111 | 119.4 | 94.8 | 104.9 |

EXAMPLE 13

| Action of grass or lawns | | | | | | | |
|---|---|---|---|---|---|---|---|
| | | | | 19 days after treatment | | | |
| | Application rate | First cutting, growth height | | dry substance | | Observations | First cutting, chlorophyll content |
| Active ingredient | kg/ha | cm | relative | g | relative | (color) | g Ca + b/100 g TS |
| Control | — | 25.5 | 100 | 12.5 | 100 | normal green | 1.33 |
| M | 0.25 | 25.0 | 98.0 | 10.5 | 84.0 | normal green | — |

-continued

| Active ingredient | Application rate kg/ha | First cutting, growth height cm | relative | 19 days after treatment dry substance g | relative | Observations (color) | | First cutting, chlorophyll content g Ca + b/100 g TS |
|---|---|---|---|---|---|---|---|---|
| 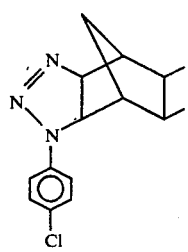 | 0.5 | 24.5 | 96.0 | 10.5 | 84.0 | normal green | | — |
| | 1.0 | 20.0 | 78.4 | 7.3 | 58.4 | normal green | | — |
| | 2.0 | 16.0 | 62.7 | 6.0 | 48.0 | lighter green | reddish brown in places | 1.11 |
| | 4.0 | 12.5 | 49.0 | 4.5 | 36.0 | lighter green | | — |
| | 0.25 | 26.0 | 101.9 | 10.7 | 85.6 | normal green | | — |
| | 0.5 | 24.0 | 94.1 | 8.6 | 68.8 | normal green | | — |
| | 1.0 | 19.0 | 74.5 | 7.0 | 56.0 | normal green | | — |
| | 2.0 | 16.0 | 62.7 | 4.8 | 38.4 | dark green | | — |
| | 4.0 | 10.5 | 41.1 | 3.1 | 24.8 | dark green | | — |
| 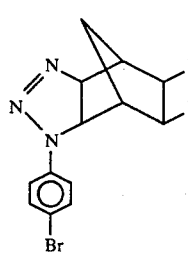 | 0.25 | 25.0 | 98.0 | 12.8 | 102.4 | normal green | | — |
| | 0.5 | 24.0 | 94.1 | 11.4 | 91.2 | normal green | | — |
| | 1.0 | 21.5 | 84.2 | 8.4 | 67.2 | normal green | | — |
| | 2.0 | 18.0 | 70.5 | 6.3 | 50.4 | dark green | | 1.40 |
| | 4.0 | 12.5 | 49.0 | 4.1 | 32.8 | dark green | | — |

EXAMPLE 14

Long-term action on lawns

A further experiment was carried out on lawns under the same conditions as in Example 13. To investigate the long-term action of the compounds of the invention, the growth of the grass was observed for 3 cuttings after treatment, and in the period of renewed growth after each cutting the shortening effect and the corresponding decrease in dry substance were ascertained. The good long-term action of the agents examined is apparent from the following table. The prior art compound used for comparison purposes was the diethanolamine salt of 3-trifluoromethylsulfonamido-p-acetotoluidide (S; Proc. Northeast. Weed Sci. Soc., 29, 403–408, 1975).

EXAMPLE 14

Long-term action on lawns

| Active ingredient | Application rate kg/ha | First cutting growth height cm | relative | green weight g | relative | Second cutting growth height cm | relative | green weight g | relative | Third cutting green weight g | relative |
|---|---|---|---|---|---|---|---|---|---|---|---|
| Control | — | 18.0 | 100 | 35.3 | 100 | 14.7 | 100 | 26.7 | 100 | 15.2 | 100 |
| S | 0.5 | 14.5 | 80.6 | 26.7 | 75.6 | 14.0 | 95.2 | 27.3 | 102.2 | 15.6 | 102.6 |
| | 1.0 | 13.0 | 72.2 | 23.0 | 65.2 | 12.5 | 85.0 | 27.6 | 103.4 | 15.0 | 98.6 |
| | 2.0 | 10.5 | 58.3 | 12.6 | 35.7 | 9.5 | 64.6 | 20.1 | 75.3 | 13.7 | 90.1 |
| | 4.0 | 9.0 | 50.0 | 9.4 | 26.6 | 4.5 | 30.6 | 9.6 | 36.0 | 10.4 | 68.4 |
| 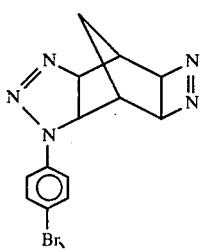 | 0.5 | 14.5 | 80.6 | 25.5 | 72.2 | 14.5 | 98.6 | 27.8 | 104.1 | 16.5 | 108.6 |
| | 1.0 | 12.5 | 69.5 | 24.4 | 69.1 | 11.5 | 78.2 | 25.1 | 94.0 | 16.5 | 108.6 |
| | 2.0 | 11.0 | 61.1 | 22.0 | 62.3 | 8.0 | 54.4 | 18.7 | 70.0 | 14.0 | 92.1 |
| | 4.0 | 10.5 | 58.3 | 16.5 | 46.7 | 7.0 | 47.6 | 13.2 | 49.4 | 10.3 | 67.8 |

-continued

Long-term action on lawns

| Active ingredient | Application rate kg/ha | First cutting growth height cm | First cutting growth height relative | First cutting green weight g | First cutting green weight relative | Second cutting growth height cm | Second cutting growth height relative | Second cutting green weight g | Second cutting green weight relative | Third cutting green weight g | Third cutting green weight relative |
|---|---|---|---|---|---|---|---|---|---|---|---|
| [structure: triazole-norbornane with NH-NH and 4-Cl-phenyl] | 0.5 | 16.5 | 91.7 | 28.8 | 81.6 | 12.5 | 85.0 | 27.2 | 101.9 | 17.2 | 113.2 |
| | 1.0 | 13.5 | 75.0 | 21.3 | 60.3 | 9.0 | 61.2 | 20.5 | 76.8 | 15.1 | 99.3 |
| | 2.0 | 11.5 | 63.9 | 17.2 | 48.7 | 7.5 | 51.0 | 16.2 | 60.7 | 12.5 | 82.2 |
| | 4.0 | 9.0 | 50.0 | 13.9 | 39.4 | 5.0 | 34.0 | 10.2 | 38.2 | 9.8 | 64.5 |
| [structure: triazole-norbornane with N=N and phenyl-S-N] | 0.5 | 18.5 | 102.8 | 31.8 | 90.1 | 14.0 | 95.2 | 28.8 | 107.9 | 15.5 | 102.0 |
| | 1.0 | 16.5 | 91.7 | 27.1 | 76.8 | 13.0 | 88.4 | 25.8 | 96.6 | 15.3 | 100.7 |
| | 2.0 | 14.5 | 80.6 | 20.3 | 57.5 | 9.0 | 61.2 | 19.1 | 71.5 | 12.8 | 84.2 |
| | 4.0 | 12.5 | 69.5 | 19.5 | 55.2 | 7.0 | 47.6 | 16.8 | 62.9 | 12.8 | 84.2 |
| [structure: triazole-norbornane with N=N and 4-F-phenyl] | 0.5 | 15.0 | 83.3 | 23.1 | 65.4 | 10.0 | 68.0 | 21.8 | 81.6 | 14.6 | 96.1 |
| | 1.0 | 12.5 | 69.5 | 20.5 | 58.1 | 9.0 | 61.2 | 21.4 | 80.1 | 13.5 | 88.8 |
| | 2.0 | 7.5 | 41.7 | 9.8 | 27.8 | 5.0 | 34.0 | 10.1 | 37.8 | 9.5 | 62.5 |
| | 4.0 | 6.5 | 36.1 | 7.9 | 22.4 | 2.0 | 13.6 | 7.1 | 26.6 | 7.9 | 52.0 |
| [structure: triazole-norbornane with N=N and 2-CH3-phenyl] | 0.5 | 14.0 | 77.8 | 26.8 | 75.9 | 13.0 | 88.4 | 23.5 | 88.0 | 16.5 | 108.6 |
| | 1.0 | 14.0 | 77.8 | 25.5 | 72.2 | 12.5 | 85.0 | 22.0 | 82.4 | 16.3 | 107.2 |
| | 2.0 | 12.5 | 69.5 | 20.0 | 56.7 | 22.0 | 74.8 | 21.4 | 80.1 | 15.7 | 103.3 |
| | 4.0 | 9.5 | 52.8 | 13.2 | 37.4 | 7.5 | 51.0 | 15.3 | 57.3 | 13.9 | 91.4 |

EXAMPLE 15

Action on individual grasses

Under the same conditions as in Example 13 the two grasses Festuca rubra and Poa praetensis (both components of the lawn mixture used in Example 13) were grown in a neutral sandy loam. The growth height was measured 3 weeks after treatment with the active ingredients. The results given below demonstrate the shortening effect of the compounds of the invention; Poa praetensis is influenced more strongly than Festuca rubra.

EXAMPLE 15

Influence on the growth height of the grasses Festuca rubra and Poa praetensis

| Active ingredient | Application rate kg/ha | Festuca rubra growth height cm | Festuca rubra relative | Poa praetensis growth height cm | Poa praetensis relative |
|---|---|---|---|---|---|
| Control | — | 27.5 | 100 | 22.5 | 100 |
| M | 0.5 | 28.0 | 101.8 | 23.0 | 102.2 |

-continued

Influence on the growth height of the grasses Festuca rubra and Poa praetensis

| Active ingredient | Application rate kg/ha | Festuca rubra growth height cm | Festuca rubra relative | Poa praetensis growth height cm | Poa praetensis relative |
|---|---|---|---|---|---|
| [structure: triazole-norbornane with 4-Cl-phenyl] | 1.0 | 28.5 | 103.6 | 22.0 | 97.8 |
| | 2.0 | 26.5 | 96.4 | 22.0 | 97.8 |
| | 0.5 | 27.0 | 98.2 | 20.0 | 88.9 |
| | 1.0 | 25.5 | 92.7 | 20.0+ | 88.9 |
| | 2.0 | 23.5 | 85.5 | 15.5+ | 68.9 |

-continued
Influence on the growth height of the grasses Festuca rubra and Poa praetensis

| Active ingredient | Application rate kg/ha | Festuca rubra growth height cm | relative | Poa praetensis growth height cm | relative |
|---|---|---|---|---|---|
| 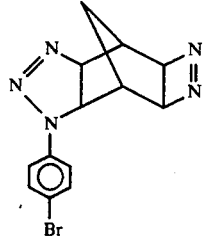 | 0.5 | 29.5 | 107.3 | 19.0 | 84.4 |
| | 1.0 | 27.5 | 100.0 | 17.5+ | 77.8 |
| | 2.0 | 25.5 | 92.7 | 14.0+ | 62.2 |

+ plants a darker green

EXAMPLE 16

Action of soybeans (hydroponic treatment)

Young soybean plants grown in quartz sand were transferred to hydroponic treatment in 4 liter vessels and provided with a sufficient supply of nutrient solution and trace elements. The active ingredients were added (0.25 mg/vessel=0.06 ppm; 1.0 mg/vessel=0.25 ppm; 2.5 mg/vessel=0.63 ppm) at a plant height of approx. 22 cm. The plants were in continuous contact with the active ingredients. During the growth period of 4 weeks the growth height of the treated plants was considerably reduced, compared with the control. The roots were also shorter, but the plants had more and stronger shoots. The results are given below.

EXAMPLE 16

Influence on the growth of roots and shoots of soybeans (hydroponic treatment)

| Active ingredient | Application rate ppm | Shoot length cm | rel. | dry substance g | rel. | Root length cm | rel. | dry substance g | rel. |
|---|---|---|---|---|---|---|---|---|---|
| Control | — | 74.3 | 100 | 41.1 | 100 | 30.3 | 100 | 13.3 | 100 |
| 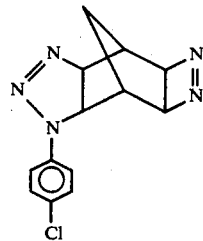 | 0.06 | 70.7 | 95.4 | 39.0 | 94.9 | 28.3 | 93.4 | 13.5 | 97.1 |
| | 0.25 | 62.3 | 84.1 | 31.5 | 76.6 | 24.7 | 81.5 | 13.2 | 95.0 |
| | 0.63 | 51.7 | 69.8 | 26.6 | 64.7 | 24.7 | 81.5 | 15.0 | 107.9 |

EXAMPLE 17a–c

Action on soybeans, field beans and sunflowers

The action on soybeans, field beans and sunflowers was examined under the same conditions as in Example 16. The shoots and roots of all 3 crop plants were considerably shortened. Whereas in the shoots the dry substance was reduced commensurately with the shortening, the dry substance in the roots rose (particularly in soybeans) as the concentration increased. The results are given below.

EXAMPLE 17a

Action on soybeans (hydroponic treatment)

| Active ingredient | Application rate ppm | Shoot length cm | rel. | dry substance g | rel. | Root length cm | rel. | dry substance g | rel. |
|---|---|---|---|---|---|---|---|---|---|
| Control | — | 36.7 | 100 | 5.8 | 100 | 28.7 | 100 | 1.1 | 100 |
| 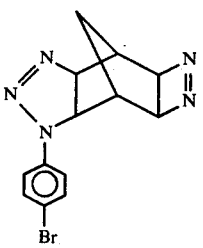 | 0.06 | 33.0 | 89.9 | 5.4 | 93.1 | 21.7 | 75.6 | 1.5 | 136.4 |
| | 0.25 | 21.7 | 59.1 | 4.9 | 84.5 | 20.0 | 69.7 | 1.5 | 136.4 |
| | 0.63 | 19.0 | 51.8 | 3.9 | 67.2 | 20.0 | 69.7 | 2.1 | 190.9 |

EXAMPLE 17b

Action of field beans (hydroponic treatment)

| Active ingredient | Application rate ppm | Shoot length cm | rel. | dry substance g | rel. | Root length cm | rel. | dry substance g | rel. |
|---|---|---|---|---|---|---|---|---|---|
| Control | — | 73.0 | 100 | 16.9 | 100 | 41.3 | 100 | 6.2 | 100 |

Action of field beans (hydroponic treatment)

| Active ingredient | Application rate ppm | Shoot length cm | rel. | Shoot dry substance g | rel. | Root length cm | rel. | Root dry substance g | rel. |
|---|---|---|---|---|---|---|---|---|---|
| 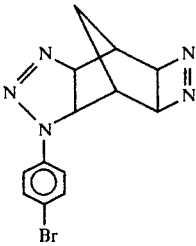 | 0.06 | 69.7 | 95.5 | 14.5 | 85.8 | 28.3 | 68.5 | 3.8 | 63.3 |
| | 0.25 | 67.3 | 92.2 | 14.5 | 85.8 | 28.3 | 68.5 | 5.3 | 85.5 |
| | 0.63 | 56.7 | 77.7 | 13.0 | 76.9 | 25.0 | 60.5 | 6.0 | 96.8 |

EXAMPLE 17c

Action on sunflowers (hydroponic treatment)

| Active ingredient | Application rate ppm | Shoot length cm | rel. | Shoot dry substance g | rel. | Root length cm | rel. | Root dry substance g | rel. |
|---|---|---|---|---|---|---|---|---|---|
| Control | — | 41.3 | 100 | 6.4 | 100 | 20.0 | 100 | 1.5 | 100 |
| 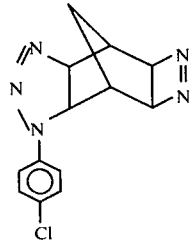 | 0.06 | 35.0 | 84.7 | 6.3 | 98.4 | 18.7 | 93.5 | 1.5 | 100 |
| | 0.25 | 27.3 | 66.1 | 5.3 | 82.8 | 16.7 | 83.5 | 1.4 | 93.3 |
| | 0.63 | 27.3 | 66.1 | 5.2 | 81.3 | 12.7 | 63.5 | 1.6 | 106.7 |

EXAMPLE 18

Action on cotton

Cotton plants were subjected to hydroponic treatment under the same conditions as in Example 16. The active ingredients were added (1.25 mg/vessel=0.3 ppm and 5 mg/vessel=1.25 ppm) at a height of the plants of 15 to 18 cm. During the 4 week growth period it was not only observed that the treated plants were considerably shortened, but also that the buds of the control plants and those treated with CCC withered in the nascent stage and dropped off, whereas the other treated plants developed a surprisingly large number of distinct squares. The results below are averages from 3 vessels, each of 3 plants.

EXAMPLE 18

Induction of flowering and influence on the growth height of cotton (hydroponic treatment)

| Active ingredient | Application rate ppm | Shoot length cm | rel. | No. of squares per vessel (3 plants) |
|---|---|---|---|---|
| Control | — | 47.2 | 100 | 0 |
| CCC | 0.3 | 36.2 | 76.7 | 0 |
| | 1.25 | 34.8 | 73.8 | 0 |
| 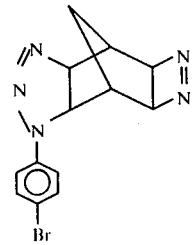 | 0.3 | 40.2 | 85.2 | 4.0 |
| | 1.25 | 27.8 | 58.9 | 8.7 |
| | 0.3 | 41.9 | 88.8 | 2.6 |
| | 1.25 | 30.9 | 65.5 | 8.3 |

EXAMPLE 19

Action on soybeans in a vegetation experiment in sandy soil

Soybean plants of the Gieso variety were grown in a neutral sandy loam. Fertilization took place at the time of sowing, with 0.5 g N as ammonium nitrate and 1.0 g P₂O₅ as secondary potassium phosphate. The active ingredients were applied to the soil at rates of 3 and 6 kg/ha at a growth height of the plants of 10 to 12 cm.

After 4 weeks, the treated plants were much shorter than the control, and looked more compact as a result of the different angle of the leaves. The results are given below. The prior art compound used for comparison purposes was 2,3,5-triiodobenzoic acid (T; U.S. Pat. No. 2,978,838).

EXAMPLE 19

Action on soybeans in a vegetation experiment in a sandy loam

| Active ingredient | Application rate kg/ha | Growth height cm | relative |
|---|---|---|---|
| Control | — | 23.0 | 100 |
| T | 0.125 | 23.5 | 102.2 |
|  | 0.375 | 25.0 | 108.7 |
|  | 0.750 | 23.0 | 100.0 |
| 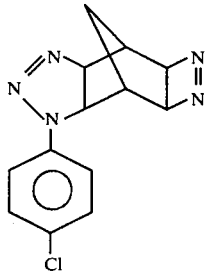 | 3.0 | 15.0 | 65.2 |
|  | 6.0 | 14.0 | 60.9 |
| 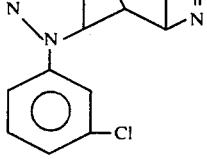 | 3.0 | 17.5 | 76.1 |
|  | 6.0 | 14.5 | 63.0 |
| 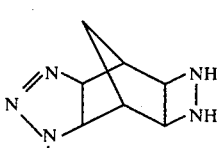 | 3.0 | 13.5 | 58.7 |
|  | 6.0 | 12.5 | 54.4 |
| 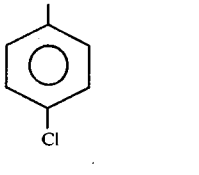 | 3.0 | 17.5 | 76.1 |
|  | 6.0 | 13.5 | 58.7 |
| 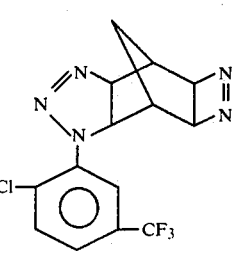 | 3.0 | 14.0 | 60.9 |
|  | 6.0 | 14.0 | 60.9 |
| 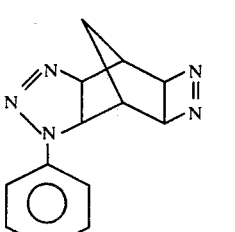 | 3.0 | 21.0 | 91.3 |
|  | 6.0 | 17.0 | 73.9 |
| 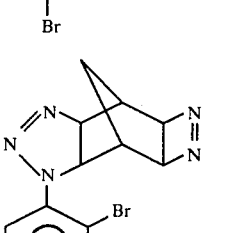 | 3.0 | 17.0 | 73.9 |
|  | 6.0 | 16.0 | 69.6 |

EXAMPLE 20

Action on sugar beet

Sugar beets of the KAWpoly variety were grown in a neutral sandy loam in large pots. Fertilization with 1.5 g N as ammonium nitrate and 1 g P₂O₅ as secondary potassium phosphate took place at the time of sowing. At a plant height of 16 to 18 cm the leaves were treated twice, once with 0.5 kg/ha and once with 1 kg/ha; in each case, 4 pots formed a variation of the experiment. After harvesting, the yield and sugar content in the beets and the lower stems were found to have been improved by the treatment. The results are given in the following table.

EXAMPLE 20

| Influence on yield and sugar content of sugar beet | | | | | | |
|---|---|---|---|---|---|---|
| Active ingredient | Application rate kg/ha | Yield g dry substance/vessel | rel. | Sugar content % in dry substance | rel. | Sugar content of lower stems % in dry substance | rel. |
| Content 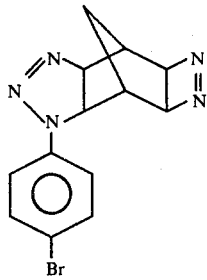 | — | 12.4 | 100 | 50.3 | 100 | 22.7 | 100 |
| | 0.5 | 13.04 | 107.4 | 51.0 | 101.4 | 22.9 | 100.9 |
| | 1.0 | 14.39 | 118.5 | 52.2 | 103.8 | 25.8 | 113.6 |

EXAMPLE 21

Influence on the sugar content of sugar beet in the open

The active ingredient was applied to small plots in an ordinary beet field to demonstrate the positive influence on sugar production under field conditions. The crop plant was Beta vulgaris sap. altissima, variety "Kleinwanzleben KAWPoly". The soil was a sandy loam (1.5% organic substance, pH 5.7). Mineral fertilization totalled 400 kg N, 100 kg $P_2O_5$, and 100 kg $K_2O$ per hectare. For chemical weed control, 2.5 kg/ha of 1-phenyl-4-amino-5-chloropyridazone-(6) was applied before emergence of the beet plants. Aphids were controlled with dimethoate (0,0-dimethyl-S-(N-methylcarbonylmethyl)-phosphorus dithioate). Sowing took place on March 10, 1975. The beets were lifted comparatively early on September 29, 1975. The active ingredient was applied with the aid of spraying equipment with fine nozzles, mounted on a tractor. The amount of water used for dispersion purposes was 780 liters/ha. Treatment was effected on 2 different dates and on different plots:

I. the beet had 5 to 7 true leaves;

II. five weeks before harvesting, on the well developed plants.

The sugar content was determined from fresh beets immediately after lifting.

The following results may be recorded:
(1) There was no impairment of the beets during the growth period.
(2) The sugar yields overall were low as a result of the early lifting. However, the sugar content was significantly improved by the active ingredient (cf. table).

The results with sugar beet are an indication of the increased production of desirable plant constituents as a consequence of treatment with a representative of the class of compounds described.

EXAMPLE 21

| Increase in the sugar content of sugar beet by chemical treatment in the open | | | | |
|---|---|---|---|---|
| Active ingredient | Application rate kg/ha | Date treated | Sugar content in freshly lifted beet absolute % | relative increase |
| Control | — | — | 12.6 a[++] | 100 |
| | 2.0 | I[+] | 14.35 b | 113 |
| | 2.0 | II | 13.85 ab | 110 |

[+] I = 20.05.75 Harvest: 29.09.75
II = 21.08.75
[++] Values which have letters in common are not significantly different (Duncan's new multiple range test, level 0.05%).

EXAMPLE 22

Action on tomatoes

Tomatoes were grown in the greenhouse in glass dishes 11.5 cm in diameter containing a peat substrate which was provided with an adequate supply of nutrients. The active ingredients were sprayed onto the leaves in conventional manner at a plant height of 9 to 12 cm. After 14 days the treated plants were shorter than the control, and had a deeper color.

| Active ingredient | Application rate kg/ha | Plant height cm | relative |
|---|---|---|---|
| Control | — | 27.2 | 100 |

-continued

| Active ingredient | Application rate kg/ha | Plant height cm | relative |
|---|---|---|---|
| [structure: triazole-diazo bicyclic with 4-Cl-phenyl] | 1.5 | 24.3 | 89.3 |
|  | 3.0 | 20.3 | 74.6 |
|  | 6.0 | 14.0 | 51.5 |
| [structure: triazole-diazo bicyclic with 4-Br-phenyl] | 1.5 | 25.0 | 91.9 |
|  | 3.0 | 22.7 | 83.5 |
|  | 6.0 | 15.3 | 56.2 |

EXAMPLE 23

Action on rice

Rice was grown in the greenhouse under the same conditions as in Example 22. At a growth height of 11 to 13 cm the active ingredients were sprayed onto the leaves in the usual manner. The plants were measured after 66 days. The treated plants were up to 30% shorter than the control.

| Active ingredient | Application rate kg/ha | Plant height cm | relative |
|---|---|---|---|
| Control | — | 40.6 | 100 |
| CCC | 1.0 | 38.0 | 93.6 |
|  | 2.0 | 40.5 | 99.8 |
|  | 4.0 | 38.5 | 94.8 |
|  | 6.0 | 40.0 | 98.5 |
| [structure: 4-Cl-phenyl] | 1.0 | 35.0 | 86.2 |
|  | 2.0 | 33.0 | 81.3 |
|  | 4.0 | 29.5 | 72.7 |
|  | 6.0 | 28.5 | 70.2 |
| [structure: 4-Br-phenyl] | 1.0 | 37.0 | 91.1 |
|  | 2.0 | 37.0 | 91.1 |
|  | 4.0 | 34.5 | 85.0 |
|  | 6.0 | 33.5 | 82.5 |

EXAMPLE 24

Action on sunflowers

Sunflowers were grown under the same conditions as in Example 22. The active ingredients were applied both to the soil and to the leaves. Both methods of treatment resulted in much shorter plants than the control.

| Active ingredient | Application rate kg/ha | Plant height cm | relative |
|---|---|---|---|
| (A) Soil treatment |  |  |  |
| Control | — | 36.3 | 100 |
| CCC | 3.0 | 40.0 | 110 |
|  | 12.0 | 36.0 | 99 |
| [structure: 4-Cl-phenyl] | 3.0 | 26.5 | 73 |
|  | 12.0 | 15.5 | 43 |
| [structure: 4-Br-phenyl] | 3.0 | 30.5 | 84 |
|  | 12.0 | 22.5 | 62 |
| (B) Leaf treatment |  |  |  |
| Control | — | 38.3 | 100 |
| CCC | 1.5 | 38.0 | 99 |
|  | 6.0 | 32.5 | 85 |
| [structure: 4-Cl-phenyl] | 1.5 | 30.0 | 78 |
|  | 6.0 | 25.5 | 67 |
| [structure: 4-Br-phenyl] | 1.5 | 33.0 | 86 |
|  | 6.0 | 30.0 | 78 |

EXAMPLE 25

Herbicidal action

The new compounds listed in Tables 1 to 3 below have proved to be effective in the control of unwanted plants. The following test method was employed.

Paraffined paper cups having a volume of 170 cm³ were filled with a sandy loam, and the seeds of the test plants sown therein, separated by species. (The species are also listed below.)

In the first group, treatment was effected immediately after sowing and before germination of the seeds (preemergence treatment=soil treatment). Shallow sown seeds not completely covered with soil came into contact with the active ingredients. In the second group, the plants were treated postemergence (=leaf treatment) at a growth height of from 2 to 8 cm, depending on the rate of growth and shape of the species concerned. The compounds were suspended or emulsified in water and applied with the aid of fine nozzles. The amounts applied are given in Tables 1 to 3. The soil and plants were thoroughly sprinkler irrigated for the duration of the experiment. The cups were placed in the greenhouse and kept in the temperature range 12°–25° C. or 18°–35° C., depending on the temperature requirements of the various species. After 2 to 6 weeks the action was assessed visually on a 0 to 100 scale, 0 denoting no damage and 100 denoting plants not germinated or completely destroyed.

List of plants employed in Tables 1 to 3:

| Latin name | English name |
| --- | --- |
| Alopecurus myosuroides | Blackgrass |
| Cynodon dactylon | Bermudagrass |
| Cyperus esculentus | Yellos nutsedge |
| Datura stramonium | Jimson weed |
| Digitaria sanguinalis | Hairy crabgrass |
| Echinochloa crus-galli | Barnyardgrass |
| Euphorbia spp. usually E. geniculata | Spurge family |
| Eleusine indica | Goosegrass |
| Galium aparine | Catchweed bedstraw |

-continued

| Latin name | English name |
| --- | --- |
| Ipomoea spp. usually I. lacunosa | Morningglory |
| Matricaria chamomilla | Wild chamomile |
| Panicum virgatum | Switchgrass |
| Poa annua | Annual bluegrass |
| Setaria faberii | Giant foxtail |
| Sinapis alba | White mustard |
| Solanum nigrum | Black nightshade |
| Sorghum halepense | Johnsongrass |
| Stellaria media | Chickweed |

Results (Tables 1, 2, 3)

(1) The herbicidal action of the new compounds in combatting and controlling unwanted plant growth was confirmed. This action was observed on monocotyledonous and dicotyledonous species, and with pre- and postemergence application. Representatives of widely varying botanical families were investigated.

(2) Herbaceous crop plants were not very resistant to the compounds given in Tables 1 to 3 (soil and leaf treatment). However, the compounds are suitable for removing and suppressing unwanted plants when a technique is employed in crop plants in which the active ingredients do not come into direct contact with the young leaves of the crop plants (postdirected spray, lay-by treatment, granulation of the active ingredients). It is also possible to apply the compounds to perennial species after cutting or during dormancy. A further field is weed control in woody crop plants such as berry bushes and trees of all kinds. Unwanted plants can also be removed or suppressed in loci where no account need be taken of crop plants.

TABLE 1

Herbicidal action - preemergence application

| Active ingredient | Application rate kg/ha | Alopecurus myosuroides | Cynodon dactylon | Cyperus esculentus | Digitaria sanguinalis | Euphorbia spp. | Ipomoes spp. |
| --- | --- | --- | --- | --- | --- | --- | --- |
| 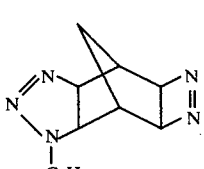 | 2.0 | — | 70 | 27 | 100 | — | 50 |
|  | 4.0 | 85 | 90 | 55 | — | — | 60 |
| 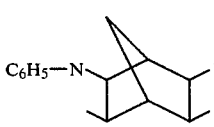 | 2.0 | 70 | 65 | 45 | 70 | 90 | — |
|  | 4.0 | 83 | 90 | 60 | 100 | 100 | 29 |
| 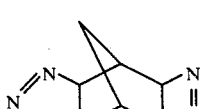 | 2.0 | 55 | 80 | 55 | — | — | 0 |
|  | 4.0 | 70 | 100 | 55 | — | — | 10 |

TABLE 1-continued

Herbicidal action - preemergence application

| Active ingredient | Application rate kg/ha | Matricaria chamomilla | Panicum virgatum | Poa annua | Setaria faberii | Sinapis alba | Sorghum halepense | Stellaria media |
|---|---|---|---|---|---|---|---|---|
| (structure with p-tolyl-N-triazole bicyclic) | 2.0 | 40 | 83 | 0 | 100 | 90 | 78 | |
| | 4.0 | 40 | 100 | 0 | 100 | 100 | 75 | |
| (phenylsulfonyl-N bicyclic diazo) | 2.0 | 80 | 90 | 0 | 68 | 65 | 78 | |
| | 4.0 | 80 | 100 | 0 | 90 | 90 | — | |
| (C$_6$H$_5$-N triazole bicyclic) | 2.0 | 95 | 100 | 95 | 97 | 99 | 75 | 100 |
| | 4.0 | — | — | — | 100 | 100 | 100 | — |
| (C$_6$H$_5$—N bicyclic diazo) | 2.0 | 95 | 100 | 57 | 59 | 74 | 74 | 100 |
| | 4.0 | — | — | — | 65 | 100 | 78 | — |
| (CH$_2$-C$_6$H$_5$ N-triazole bicyclic) | 2.0 | — | — | — | 80 | 80 | 90 | — |
| | 4.0 | — | — | — | 90 | 95 | 90 | — |
| (p-tolyl-N-triazole bicyclic) | 2.0 | — | — | 65 | 55 | 98 | 55 | — |
| | 4.0 | — | — | — | 100 | — | 55 | — |
| (phenylsulfonyl-N bicyclic diazo) | 2.0 | — | — | 70 | 40 | 90 | 53 | — |
| | 4.0 | — | — | — | 100 | — | 50 | — |

0 = no damage
100 = complete destruction

TABLE 2

Herbicidal action of a new compound and comparative agents - pre- and postemergence application

| Active ingredient | Application rate kg/ha | Application method | Alopecurus myosuroides | Echinochloa crus galli | Galium aparine | Sinapis alba |
|---|---|---|---|---|---|---|
| 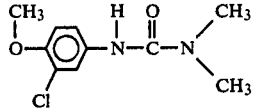 prior art (Belgian 668,018) | 1.0 | PRE | 0 | 80 | — | 90 |
| | 2.0 | PRE | 0 | 90 | — | 90 |
| | 1.0 | POST | 70 | 100 | — | 100 |
| | 2.0 | POST | 70 | 100 | — | 100 |
| | 4.0 | POST | — | — | 50 | — |
| 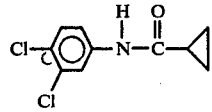 prior art (Farm Chemical Handbook 1975, Meister Publishing Co, USA, p. D50 | 1.0 | PRE | 0 | 80 | — | 60 |
| | 2.0 | PRE | 0 | 90 | — | 60 |
| | 1.0 | POST | 80 | 100 | — | 100 |
| | 2.0 | POST | 80 | 100 | — | 100 |
| | 4.0 | POST | — | — | 0 | — |
| 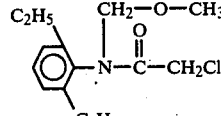 prior art (Chem. Week, 26.7.1972, p. 21) | 1.0 | PRE | 20 | 100 | — | 0 |
| | 2.0 | PRE | 78 | 100 | — | 0 |
| | 1.0 | POST | 40 | 98 | — | 0 |
| | 2.0 | POST | 50 | 98 | — | 0 |
| | 4.0 | POST | — | — | 0 | — |
| 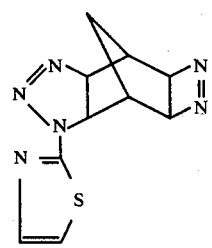 | 1.0 | PRE | 80 | 85 | — | 100 |
| | 2.0 | PRE | 95 | 85 | — | 100 |
| | 1.0 | POST | 30 | 95 | — | 100 |
| | 2.0 | POST | 70 | 100 | — | 100 |
| | 4.0 | POST | — | — | 50 | — |

0 = no damage
100 = complete destruction

TABLE 3

Herbicidal action of new compounds and comparative agents - pre- and postemergence application

| Active ingredient | Application rate kg/ha | Application method | Alopecurus myosuroides | Datura stramonium | Digitaria sanguinalis | Eleusine indica |
|---|---|---|---|---|---|---|
| 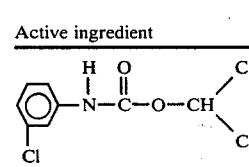 prior art (German 833,274) | 2.0 | PRE | 95 | — | — | — |
| | 4.0 | PRE | 95 | — | — | — |
| | 8.0 | PRE | 98 | — | — | — |
| | 2.0 | POST | 25 | 30 | 80 | 50 |
| | 4.0 | POST | 25 | 40 | 80 | 50 |
| | 8.0 | POST | 30 | 60 | 90 | 50 |
| prior art (German Printed Application DAS 1,142,251) | 2.0 | PRE | 30 | — | — | — |
| | 4.0 | PRE | 25 | — | — | — |
| | 8.0 | PRE | 25 | — | — | — |
| | 2.0 | POST | 15 | 95 | 50 | 40 |
| | 4.0 | POST | 22 | 95 | 70 | 50 |
| | 8.0 | POST | 38 | 100 | 90 | 50 |

TABLE 3-continued
Herbicidal action of new compounds and comparative agents - pre- and postemergence application

| Active ingredient | Application rate kg/ha | Application method | | | |
|---|---|---|---|---|---|
| 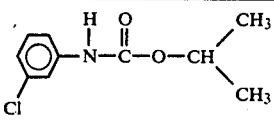 CH$_2$=CH—CH$_2$\N—C(=O)—CH$_2$Cl / CH$_2$=CH—CH$_2$  prior art (U.S. Pat. No. 2,864,683) | 2.0<br>4.0<br>8.0<br>2.0<br>4.0<br>8.0 | PRE<br>PRE<br>PRE<br>POST<br>POST<br>POST | 68<br>85<br>98<br>28<br>38<br>35 | —<br>—<br>—<br>10<br>20<br>60 | —<br>—<br>—<br>—<br>—<br>— |

| Active ingredient | Application rate kg/ha | Application method | Test plants and % age damage | | | |
|---|---|---|---|---|---|---|
| | | | Galium aparine | Lamium spp. | Poa annua | Solanum nigrum |
| 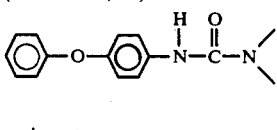 prior art (German 833,274) | 2.0<br>4.0<br>8.0<br>2.0<br>4.0<br>8.0 | PRE<br>PRE<br>PRE<br>POST<br>POST<br>POST | 88<br>80<br>88<br>0<br>0<br>10 | 72<br>90<br>95<br>50<br>50<br>90 | 100<br>100<br>100<br>30<br>30<br>42 | 85<br>85<br>90<br>22<br>22<br>38 |
| 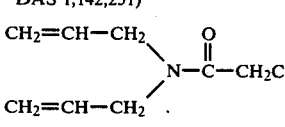 prior art (German Printed Application DAS 1,142,251) | 2.0<br>4.0<br>8.0<br>2.0<br>4.0<br>8.0 | PRE<br>PRE<br>PRE<br>POST<br>POST<br>POST | 60<br>80<br>75<br>0<br>0<br>0 | 50<br>65<br>75<br>75<br>85<br>85 | 50<br>58<br>65<br>30<br>30<br>30 | 75<br>80<br>90<br>100<br>100<br>100 |
| 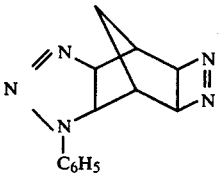 CH$_2$=CH—CH$_2$\N—C(=O)—CH$_2$Cl / CH$_2$=CH—CH$_2$  prior art (U.S. Pat. No. 2,864,683) | 2.0<br>4.0<br>8.0<br>2.0<br>4.0<br>8.0 | PRE<br>PRE<br>PRE<br>POST<br>POST<br>POST | 70<br>80<br>90<br>5<br>5<br>5 | 25<br>60<br>85<br>0<br>10<br>20 | 95<br>98<br>100<br>35<br>35<br>40 | 0<br>15<br>25<br>10<br>10<br>20 |

| Active ingredient | Application rate kg/ha | Application method | Test plants and % age damage | | | |
|---|---|---|---|---|---|---|
| | | | Alopecurus myosuroides | Datura stramonium | Digitaria sanguinalis | Eleusine indica |
| 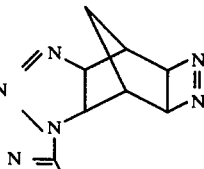 | 2.0<br>4.0<br>8.0<br>2.0<br>4.0<br>8.0 | PRE<br>PRE<br>PRE<br>POST<br>POST<br>POST | 70<br>75<br>90<br>15<br>38<br>45 | —<br>—<br>—<br>60<br>95<br>100 | —<br>—<br>—<br>60<br>70<br>80 | —<br>—<br>—<br>90<br>90<br>90 |
| 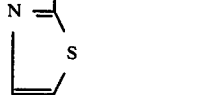 | 2.0<br>4.0<br>8.0<br>2.0<br>4.0<br>8.0 | PRE<br>PRE<br>PRE<br>POST<br>POST<br>POST | 70<br>88<br>100<br>32<br>40<br>50 | —<br>—<br>—<br>50<br>60<br>65 | —<br>—<br>—<br>60<br>60<br>80 | —<br>—<br>—<br>60<br>60<br>70 |

| Active ingredient | Application rate kg/ha | Application method | Test plants and % age damage | | | |
|---|---|---|---|---|---|---|
| | | | Galium aparine | Lamium spp. | Poa annua | Solanum nigrum |
| 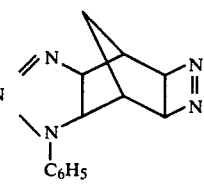 | 2.0<br>4.0<br>8.0<br>2.0<br>4.0<br>8.0 | PRE<br>PRE<br>PRE<br>POST<br>POST<br>POST | 80<br>100<br>100<br>10<br>15<br>20 | 95<br>95<br>95<br>60<br>90<br>90 | 100<br>100<br>100<br>35<br>40<br>50 | 95<br>95<br>95<br>85<br>100<br>100 |

TABLE 3-continued

Herbicidal action of new compounds and comparative agents - pre- and postemergence application

| Structure | | | | | |
|---|---|---|---|---|---|
| (structure shown) | 2.0 | PRE | 72 | 95 | 80 | 95 |
| | 4.0 | PRE | 98 | 95 | 92 | 95 |
| | 8.0 | PRE | 90 | 95 | 95 | 95 |
| | 2.0 | POST | 10 | 55 | 38 | 90 |
| | 4.0 | POST | 18 | 60 | 52 | 95 |
| | 8.0 | POST | 30 | 95 | 68 | 100 |

0 = no damage
100 = complete destruction
PRE = preemergence application
POST = postemergence application

EXAMPLE 26

90 parts by weight of compound 1 is mixed with 10 parts by weight of N-methyl-α-pyrrolidone. A mixture is obtained which is suitable for application in the form of very fine drops.

EXAMPLE 27

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 28

20 parts by weight of compound 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 29

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 30

20 parts by weight of compound 1 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 31

3 parts by weight of compound 2 is intimately mixed with 97 parts by weight of particulate kaolin. A dust is obtained containing 3% by weight of the active ingredient.

EXAMPLE 32

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 33

40 parts by weight of compound 1 is intimately mixed with 10 parts of the sodium salt of a phenolsulfonic acid-ureaformaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 34

20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

EXAMPLE 35

Further experiments were carried out in the greenhouse under the conditions described in Example 11. The plastic pots had a volume of 300 cm$^3$. As the plants which were examined liked the warmth (Euphorbia geniculata, Arachis hypogaea, Cynodon dactylon), they were kept at from 20°-30° C. Cynodon dactylon from seed was cut once and the young growth treated postemergence.

Results

Postemergence treatment with the compounds of the invention listed in Table 1 below resulted in a considerable (and desirable from the crop point of view) reduction in shoot growth in groundnuts (Arachis hypogaea)

and Bermudagrass (Cynodon dactylon). The same effect can be achieved with a preemergence application, as shown for instance in Table 2 at Euphorbia geniculata. It is particularly noteworthy that the comparative agents only act on certain plant species. By contrast, the compounds according to the invention act on a larger number of plant species. Similar effects were obtained with the new compounds in soybeans (Glycine max.), Indian corn (Zea mays) and other species.

TABLE 1

Growth-regulating action in groundnuts (*A. hypogaea*) and Bermudagrass (*C. dactylon*) - postemergence application in greenhouse

| Active ingredient | Application rate kg/ha | Arachis hypogaea cm | relative | Cynodon dactylon cm | relative |
|---|---|---|---|---|---|
| Untreated control | — | 16 | 100 | 11 | 100 |
|  | 2.0 | 9 | 56 | 4 | 36 |
|  | 1.0 | 12 | 75 | 4 | 36 |
|  | 0.5 | 13 | 81 | 4 | 36 |
|  | 2.0 | 5 | 31 | 3 | 27 |
|  | 1.0 | 7.5 | 47 | 4 | 36 |
|  | 0.5 | 8 | 50 | 4 | 36 |
|  | 0.25 | 8 | 50 | — | — |
|  | 2.0 | 10 | 62 | 6 | 54 |
|  | 1.0 | 14 | 87 | 6 | 54 |
|  | 0.5 | 14 | 87 | 7 | 64 |
|  | 2.0 | — | — | 6 | 54 |
|  | 1.0 | — | — | 7 | 64 |
|  | 0.5 | — | — | 8 | 73 |
| CH$_2$—C(O)—NH—N(CH$_3$)$_2$ / CH$_2$—COOH  prior art | 2.0 | 7 | 44 | 9 | 82 |
|  | 1.0 | 7 | 44 | 12 | 109 |
|  | 0.5 | 8 | 50 | 12 | 109 |
|  | 0.25 | 9 | 56 | — | — |
| [Cl—CH$_2$—CH$_2$—N(CH$_3$)$_3$]$^⊕$ Cl$^⊖$ prior art | 2.0 | 14 | 87 | 9 | 82 |
|  | 0.5 | 16 | 100 | 9 | 82 |

TABLE 2

Growth-regulating action in *Euphorbia geniculata* - preemergence treatment in greenhouse

| Active ingredient | Application rate kg/ha | Tests plants and growth height Euphorbia geniculata cm | relative |
|---|---|---|---|
| Untreated control | — | 11 | 100 |
|  | 1.0 | 3 | 27 |
|  | 0.5 | 5 | 45 |
|  | 0.25 | 6 | 54 |
| [Cl—CH$_2$—CH$_2$—N(CH$_3$)$_3$]$^⊕$ Cl$^⊖$ prior art | 1.0 | 9 | 82 |
|  | 0.5 | 10 | 91 |
|  | 0.25 | 10 | 91 |

TABLE 2-continued

Growth-regulating action in *Euphorbia geniculata* - preemergence treatment in greenhouse

| Active ingredient | Application rate kg/ha | Tests plants and growth height Euphorbia geniculata cm | relative |
|---|---|---|---|
| CH$_2$—C(O)—NH—N(CH$_3$)$_2$ / CH$_2$—COOH  prior art | 1.0 | 10 | 91 |
|  | 0.5 | 12 | 109 |
|  | 0.25 | 12 | 109 |

We claim:

1. A polycyclic nitrogen-containing compound of the formula

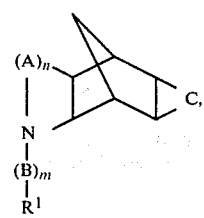

where A denotes the radical —N=N—, B denotes the radicals —SO$_2$—,

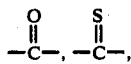

—S—, C denotes the radicals —N=N— or

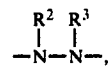

n denotes one of the integers 0 and 1, m denotes one of the integers 0 and 1, and $R^1$ denotes 1,2-benzisothiazol-5-yl, and $R^2$ and $R^3$ are identical or different and each denotes $(B)_m$-$R^4$, $R^4$ having the same meanings as $R^1$, and salts of these compounds.

2. A process for reducing crop plant growth height wherein the plants or the soil are treated with an effective amount of a polycyclic nitrogen-containing compound of the formula of claim 1 to reduce crop plant growth height.

* * * * *